(12) United States Patent
McKenzie

(10) Patent No.: US 8,591,964 B2
(45) Date of Patent: Nov. 26, 2013

(54) VACCINIUM SPECIES COMPOSITIONS

(75) Inventor: Maureen McKenzie, Soldotra (AL)

(73) Assignee: Denali Biotechnologies, Inc., Homer, AK (US)

(*) Notice: Subject to any disclaimer, the term of this patent is extended or adjusted under 35 U.S.C. 154(b) by 609 days.

(21) Appl. No.: 10/515,363

(22) PCT Filed: Apr. 3, 2003

(86) PCT No.: PCT/US03/10200
§ 371 (c)(1),
(2), (4) Date: Nov. 22, 2004

(87) PCT Pub. No.: WO03/084559
PCT Pub. Date: Oct. 16, 2003

(65) Prior Publication Data
US 2005/0175720 A1    Aug. 11, 2005

Related U.S. Application Data

(60) Provisional application No. 60/369,324, filed on Apr. 3, 2002.

(51) Int. Cl.
*A61K 36/45* (2006.01)
(52) U.S. Cl.
USPC .......................................... 424/732; 424/777
(58) Field of Classification Search
None
See application file for complete search history.

(56) References Cited

U.S. PATENT DOCUMENTS

| | | | | |
|---|---|---|---|---|
| 4,513,008 A * | 4/1985 | Revici et al. | ................ | 514/560 |
| 5,846,544 A * | 12/1998 | Al-Dahir | ..................... | 424/732 |
| 6,180,671 B1 * | 1/2001 | Freedman et al. | ............ | 514/560 |
| 6,451,341 B1 * | 9/2002 | Slaga et al. | .................... | 424/468 |

FOREIGN PATENT DOCUMENTS

RU    2137489    9/1999

OTHER PUBLICATIONS

Akiyama et al. (Neurobiology of Aging (2000), vol. 21, pp. 383-421).*
Gaisma website (www.gaisma.com/en/location/glacier-bay-national-park-and-preserve-alaska.html)—accessed Oct. 22, 2007.*
Ginsberg et al. (Nature Medicine (2007), vol. 13, No. 3. pp. 290-294).*
Heller (Edible and Poisonous Plants of Alaska (1953), University of Alaska: USA, pp. 103, 105, 107 and 109).*
https://www.cia.gov/library/publications/the-world-factbook/print/rs.html—accessed Oct. 23, 2007.*
Hulten (Flora of Alaska and Neighboring Territories: A Manual of the Vascular Plants (1968), Stanford University Press: California, pp. xii, 731-735).*
Johnson (CRC Ethnobotany Desk Reference (1999), CRC Press: USA, pp. 862-865).*
Merriam-Webster's Collegiate Dictionary (10th edition (1997), Merriam-Webster, Inc: USA, pp. 481).*
"Pathology of Tuberculosis" website (http://library.med.utah.edu/WebPath/TUTORIAL/MTB/MTB.html)—accessed Oct. 22, 2007.*
P&G website (http://www.pghsi.com/pghsi/respiratory/science_common_symptoms.html)—accessed Oct. 22, 2007.*
Smith et al. (Journal of Inflammation (2004), vol. 1, No. 3).*
Viereck (Alaska's Wilderness Medicines: Healthful Plants of the Far North (1987), Alaska Northwest Publishing Company: USA, pp. 1 and 47).*
Zevin et al. (A Russian Herbal: Traditional Remedies for Health and Healing (1997), Healing Arts Press: Canada, pp. 36-37).*
Kari. Tanaina Plantlore Dena'ina K'et'una. 1995. US Park Service: Hong Kong. pp. 60-65, 67, 68.*
Kellogg (J. Agric. Food Chem. (2010), vol. 58, pp. 3884-3900).*
Prior (J. Agric. Food Chem. (1998), vol. 46, pp. 2686-2693).*
Ewing, "The Great Alaska Nature Factbook" Portland: Alaska Northwest Books, 1996.

* cited by examiner

*Primary Examiner* — Susan Hoffman
(74) *Attorney, Agent, or Firm* — Gerry J. Elman; Elman Technology Law, P.C.

(57) ABSTRACT

This invention relates to novel compositions comprising as an active ingredient one or more berries, leaves, roots, and/or root barks obtained from one or more plant species of the genus *Vaccinium*, wherein said plant(s) is/are grown under the following conditions: a. Subject to one or more uninterrupted photoperiod(s) of at least about 18 hours to 24 hours per day for about 60 days during flowering and fruit setting; and; b. Subject to one or more uninterrupted photoperiod(s) of at least about 15 hours per day for about 30 days during fruit ripening and maturity. More particularly, said plant(s) is/are optionally grown at least 7 days past maturity. Further, the compositions of the inventive subject matter optionally may include an additional element comprising an oil from *Oncorhynchus* species. Further, said compositions may be employed to treat a variety of diseases, disorders, and conditions, as described herein.

4 Claims, 47 Drawing Sheets

Hydrophilic ORAC ranking of fruits

Figure 2

|  | ORAC$_{hydro}$ | ORAC$_{lipo}$ | ORAC$_{total}$ | ORAC$_{HO}$ | ORAC$_{ONOO-}$ |
|---|---|---|---|---|---|
|  | (mmoleTE/g) | | | (mmoleGA/g) | (mmoleTE/g) |
| Alaska blueberry | 1,160 | 45 | 1,205 | 190 | 226 |
| Cultivated blueberry-1 | 155 | N/D | N/D | 5 | 45 |
| Cultivated blueberry-2 | N/D | N/D | N/D | 90 | 125 |
| Cultivated blueberry-3 | N/D | N/D | N/D | 95 | 98 |
| Wild blueberry | 314 | N/D | N/D | 145 | 50 |
| Bilberry | 330-698* | N/D | 330-698* | 170 | N/D |
| Vitamin C (pure) | 5,513 | N/A | 5,513 | 0 | N/A |
| Vitamin E (pure) | N/A | 1,563 | 1,563 | 0 | N/A |

N/A = Not applicable; N/D = Not determined; * = Values from the literature

Separation of 10 common anthocyanins using RP-HPLC with UV detection. The structure of each compound was characterized by the Finingan LCQ Mass spec detector.

Figure 4

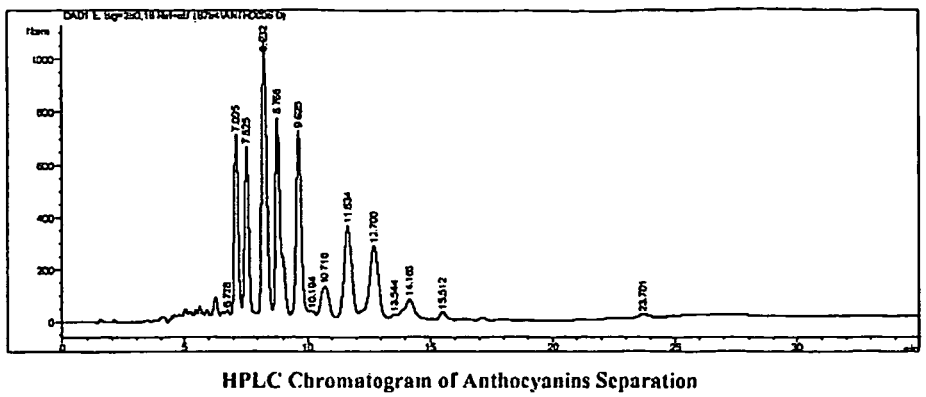

HPLC Chromatogram of Anthocyanins Separation

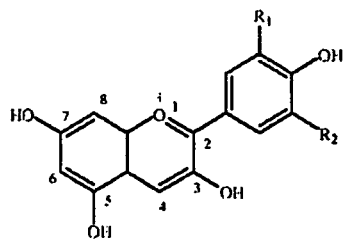

Malvidin: R1=OCH3, R2=OCH3; Petunidin: R1=OCH3, R2=OH
Peonidin: R1=OCH3, R2=H; Delphinidin: R1=OH, R2=OH
Cyanidin: R1=OH, R2=H Identity of Anthocyanin Peak and its Mass Spec Data

| Anthocyanin | Retention Time | Molecular Ion | Product Ion (aglycone) |
|---|---|---|---|
| delphinidin-3-galactoside | 7.095 | 465 | 303 |
| delphinidin-3-glucoside | 7.525 | 465 | 303 |
| cyanidin-3-galactoside | 8.249 | 449 | 287 |
| cyanidin-3-glucoside | 8.766 | 449 | 287 |
| petunidin-3-galactoside | 8.984 | 479 | 317 |
| cyanidin-3-arabinoside | 9.623 | 419 | 287 |
| petunidin-3-coumarate | 10.550 | 481 | 317 |
| petunidin-3-arabinoside | 10.771 | 449 | 317 |
| peonidin-3-galactoside | 10.771 | 463 | 301 |
| peonidin-3-glucoside | 11.631 | 463 | 301 |
| malvidin-3-galactoside | 11.631 | 493 | 331 |
| malvidin-3-glucoside | 12.695 | 493 | 331 |
| malvidin-3-arabinoside | 14.185 | 463 | 331 |

HPLC chromatogram (280 nm) of Alaskan Blueberries-wild Ethyl Acetate Fraction

Figure 6

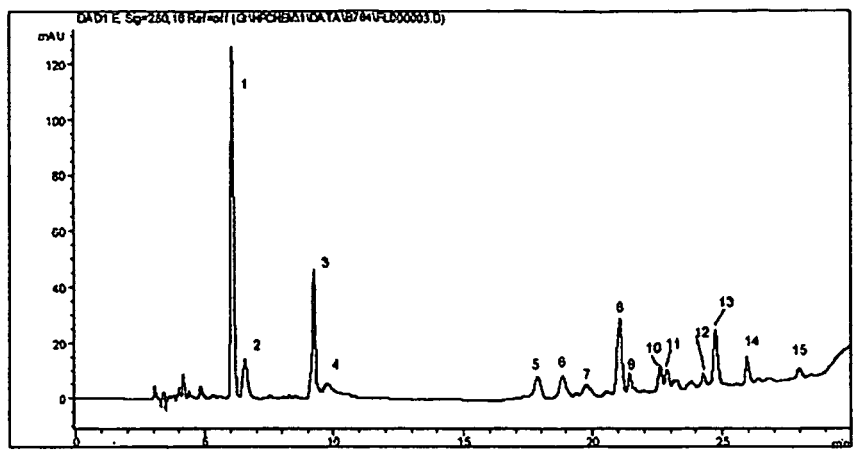

Figure 6. HPLC Chromatogram for Phenolic Profile

Table 2. Identity of Phenolic Peak and its Mass Spec Data

| Peak | Retention Time | [M+1]+ | [M-1]- | MW | Structure |
|---|---|---|---|---|---|
| 1 | 6.06 | | 153 | 154 | Protocatechuic acid |
| 2 | 6.55 | | 153 | 154 | Gentisic acid |
| 3 | 9.26 | | 289 | 290 | Catechin |
| 4 | 9.78 | | 353 | 354 | Chlorogenic acid |
| 5 | 17.87 | 321 | 319 | 320 | unknown |
| 6 | 18.86 | | 864 | 865 | Trimeric proanthocyanidin A |
| 7 | 19.74 | 481 | 479 | 480 | Myricetin-3-glucoside |
| 8 | 21.07 | 465 | 463 | 464 | Quercetin-3-glucoside |
| 9 | 21.44 | 479 | 477 | 478 | Tamarixetin-3-glucoside |
| 10 | 22.59 | 435 | 433 | 434 | Quercetin-3-arabinoside |
| 11 | 22.86 | 509 | 507 | 508 | Syringetin-3-glucoside |
| 12 | 24.30 | | 347 | 348 | unknown |
| 13 | 24.71 | 319 | 317 | 318 | Myricetin |
| 14 | 25.93 | | 445 | 446 | unknown |
| 15 | 27.96 | 303 | 301 | 302 | Quercetin |

Separation and characterization of phenolic compounds using RP-HPLC with UV detection.

Antioxidant Fingerprint for Alaskan Blueberries-wild obtained by multi-channel ECD Detector Antioxidant fingerprint of blueberries obtained by the ESA 8-channel electron chemical detector. Each peak in the chromatogram represents an antioxidant component.

Rank of Antioxidant Activity Against Hydroxyl Radicals of fruits

Figure 10

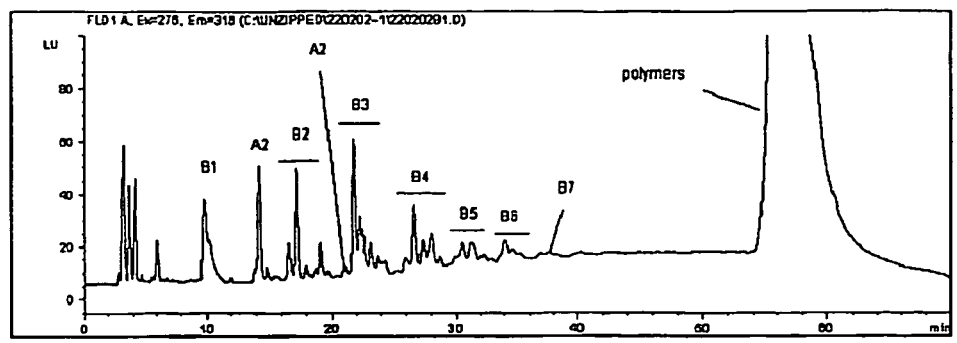

The profile of the proanthocyanins from Alaskan Blueberries. B1 are epicatechin and catechin. Peaks B2 through B7 stand for the B type procyanidin from dimers to heptamers. A2 and A3 are dimers and trimers with one A type inter-flavan linkage as reflected by the mass spectra. When compared to other blueberries, Alaskan Blueberries contains substantial high level of A2 dimers.

| Proanthocyanidins | Alaska Blueberry | *Blueberry | Cocoa | Cranberry |
|---|---|---|---|---|
| monomers | 0.37 | 0.18 | 0.65 | 0.48 |
| dimers | 1.10 | 0.46 | 0.84 | 1.53 |
| trimers | 1.16 | 0.38 | 1.03 | 1.44 |
| tetramers | 1.22 | 0.5 | 1.24 | 1.46 |
| pentamers | 1.27 | 0.47 | 1.41 | 1.39 |
| hexamers | 1.51 | 0.69 | 1.84 | 2.04 |
| heptamers | 1.05 | 0.48 | 1.13 | 1.56 |
| octamers | 1.06 | 0.61 | 1.19 | 2.17 |
| nonamers | 1.49 | 0.93 | 1.59 | NA |
| decamers | 0.71 | NA | 0.74 | NA |
| polymers | 24.49 | 15.28 | 9.81 | 20.58 |
| Total (mg/g) | 35.43 | 19.99 | 21.48 | 32.65 |

Proanthocyanidin content of Alaska blueberry, blueberry, cocoa, and cranberry.

| Peak | Retention Time | [M+1]+ | [M-1]- | MW | Structure |
|---|---|---|---|---|---|
| 1 | 3.32 | | 239 | 240 | unknown |
| 2 | 4.32 | | 239 | 240 | unknown |
| 3 | 5.72 | | 153 | 154 | Protocatechuic acid |
| 4 | 6.53 | | 153 | 154 | Gentisic acid |
| 5 | 8.29 | | 341 | 342 | unknown |
| 6 | 13.32 | 419 | | 418 | Cyanidin-3-arabinoside |
| 7 | 17.01 | 493 | | 492 | Malvidin-3-galactoside |
| 8 | 18.13 | | 479 | 480 | Myricetin-3-glucoside |
| 9 | 20.89 | 303 | 301 | 302 | Ellagic acid |
| 10 | 21.44 | 479 | 477 | 478 | Tamarixetin-3-glucoside |
| 11 | 23.89 | 319 | 317 | 318 | Myricetin |
| 12 | 26.90 | 303 | 301 | 302 | Quercetin |

VACCINIUM SPECIES COMPOSITIONS

BENEFICIAL PROPERTIES

This application claims the benefit of U.S. Provisional Patent Application No. 60/369,324, filed Apr. 3, 2002, the contents of which is hereby incorporated by reference in its entirety.

BACKGROUND OF THE INVENTION

1. Field of Invention

This invention relates to novel compositions comprising as an active ingredient one or more berries, leaves, roots, and/or root barks obtained from one or more plant species of the genus *Vaccinium*, wherein said plant(s) is/are grown under the following conditions:
   a. Subject to one or more uninterrupted photoperiod(s) of at least about 18 hours to 24 hours per day for about 60 days during flowering and fruit setting; and
   b. Subject to one or more uninterrupted photoperiod(s) of at least about 15 hours per day for about 30 days during fruit ripening and maturity.

More particularly, said plant(s) is/are optionally grown at least 7 days past maturity. Further, the compositions of the inventive subject matter optionally may include an additional element comprising an oil from *Oncorhynchus* species. Further, said compositions may be employed to treat a variety of diseases, disorders, and conditions, as described herein.

2. Background

There are approximately 90, of approximately 400 species of *Vaccinium*, that are distributed widely across the Northern Mediterranean, Southern Europe, Central Europe, Northern Europe, North Asia, South Asia, Central Asia, and East Asia. This includes approximately 50 species native to North America. Bilberry, blueberry, huckleberry, cranberry, and lingonberry fruits of the *Vaccinium* genus are a rich source of anthocyanosides, a group of red to blue plant pigments, which exist as condensed products, glycosides, of anthocyanins, known as anthocyanidins, combined usually with sugar(s) such as glucose, arabinose, and galactose.

Oxidative stress is an imbalance between oxidants and antioxidants in favor of the former, resulting in oxidative damage to molecules such as DNA, lipids, and proteins. In humans, free radicals are produced by metabolic processes, cigarette smoke, photochemical smog, pesticides, and drugs, among others. The consumption of antioxidant-rich fruits and vegetables has been associated with lower incidence and lower mortality rates of all common cancers. Further, epidemiological data, human clinical trials, and animal studies suggest that dietary antioxidants and diets rich in vegetables and fruits decrease cardiovascular disease and increase longevity. A number of studies have shown that mortality from coronary heart disease is inversely correlated with intake of substances found in certain fruits. Experts have suggested that a recommended minimum daily requirement for dietary antioxidants be established.

Some of the components present within *Vaccinium* are expected to have multiple health benefits. *V. myrtillus* scores highest among 50 fruits and vegetables in its ability to defuse damaging oxygen free radicals in the ORAC assay. ORAC analysis of commercial blueberry varieties and less common wild species from the United States and Canada has shown that consumption of one-half cup, 72.5 g, of blueberries per day increases ORAC intake by 1-3.2 mmol, depending upon the blueberry variety and maturity, making a small contribution to a healthy diet for normal individuals.

The antioxidant capacity of blueberries varies considerably. European bilberry has been reported to have the highest anthocyanin content of *Vaccinium* species, 300-698 mg anthocyanin/100 g. The total antioxidant capacity, measured as ORAC, ranges from a low of 13.9 to 44.6 mmol TE/g fresh berries in the acetonitrile extracts of the different cultivars of blueberries.

Applicant has surprisingly found that, on a fresh weight basis, Alaskan *Vaccinium* species have the highest antioxidant capacity of all *Vaccinium* berries tested to date, including European bilberry. Further, the Alaskan *Vaccinium* preparation provided in the inventive subject matter, ORAC values observed are, across the board with various radicals, unprecedented and unexpected. Applicant has found that, under the growing conditions specified in detail below, *Vaccinium* species produce an unexpectedly high level of the metabolites producing the observed ORAC, anthocyanin, proanthocyanidin, and phenolic content.

Unlike other berries, the extremely high content of anthocyanins and polyphenols in high latitude berries, exemplified by Alaskan berries allows unique formulation as a dehydrated whole food, compared to others that require extraction to concentrate beneficial molecules. The berries of the inventive subject matter provide a meaningful dose after only a mild refractance window drying step, without any additional processing or extraction. In the inventive compositions, all of the substances are retained in essentially natural ratios. As a base for product formulation, dehydrated *Vaccinium* rich in hydrophilic antioxidants is enhanced with oils from, for example, *Oncorhynchus* (salmon) species, that naturally contain lipophilic Vitamin E and other substances, including carotenoids, such as astaxanthin, and omega-3 and omega-6 fatty acids.

These factors are expected to make high latitude berries, exemplified by Alaskan berries a previously unrecognized, preferred substance for an antioxidant nutraceutical supplement. A product formulated by the inventive methods is expected to retain its preferred whole food composition, and receive less restrictive regulatory status.

SUMMARY OF THE INVENTION

The present invention relates to a composition comprising:
   i. one or more berries, leaves, roots, and/or root barks obtained from one or more plant species of the genus *Vaccinium*, wherein said plant(s) is/are grown under the following conditions:
      (a) Subject to one or more uninterrupted photoperiod(s) of at least about 18 hours to 24 hours per day for about 60 days during flowering and fruit setting; and
      (b) Subject to one or more uninterrupted photoperiod(s) of at least about 15 hours per day for about 30 days during fruit ripening and maturity.

The present invention further relates to a method for treating a disorder in an animal, which comprises administering to said animal an effective amount of a composition comprising one or more berries, leaves, roots, and/or root barks obtained from one or more plant species of the genus *Vaccinium*,
   wherein said plant(s) is/are grown under the following conditions:
   i. Subject to one or more uninterrupted photoperiod(s) of at least about 18 hours to 24 hours per day for about 60 days during flowering and fruit setting; and
   ii. Subject to one or more uninterrupted photoperiod(s) of at least about 15 hours per day for about 30 days during fruit ripening and maturity;
   and wherein said disorder is selected from the group consisting of diabetes mellitus, inflammatory disorders, ulcers, viral diseases or disorders, microbial diseases or disorders, interstitial fluid formation, capillary resistance and permeability, decreased platelet aggregation, eyestrain, diabetic retinopathy, macular degeneration, cataracts, glaucoma, cancer, obesity, atherosclerosis, and cardiovascular disease; for improving visual function by promoting dark adaptation, enhancing the activity of metabolic enzymes in the retina, improving retinal regeneration, improving visual acuity, night vision, and contrast sensitivity; and for promoting wound-healing, normal formation of connective tissue, and strengthening of capillaries.

The present invention further relates to a product produced by the process of:
  i. Growing a plant of a species of the genus *Vaccinium* under the following conditions:
    (a) Subject to one or more uninterrupted photoperiod(s) of at least about 18 hours to 24 hours per day for about 60 days during flowering and fruit setting,
    (b) Subject to one or more uninterrupted photoperiod(s) of at least about 15 hours per day for about 30 days during fruit ripening and maturity, and
    (c) Grown at least about 7 days past peak fruit ripeness;
  ii. Harvesting berries, leaves, roots, and/or root barks from said plant; and
  iii. Drying said berries, leaves, roots, and/or root barks from said plant.

The inventive subject matters also relates to a composition comprising berries obtained from one or more plant species of the genus *Vaccinium*, wherein said plant(s) is/are processed according to the following steps:
  (a) Exposed to one or more uninterrupted photoperiod(s) of at least about 18 hours to 24 hours per day for about 60 days during flowering and fruit setting;
  (b) Exposed to one or more uninterrupted photoperiod(s) of at least about 15 hours per day for about 30 days during fruit ripening and maturity;
  (c) Grown at least about 7 days past peak fruit ripeness;
  (d) Dried; and
  (e) Formulated into a therapeutic or nutritional composition having about 0.1 mg to about 100 mg per kilogram body weight of active ingredients.

BRIEF DESCRIPTION OF THE DRAWINGS

FIG. 2 is a chart which depicts ORAC values of the berries of the inventive subject matter for peroxyl radical in hydrophilic and hydrophobic conditions, as well as for hydroxyl and peroxynitrite radicals.

FIG. 4 is a graph which depicts anthocyanin profiles of a cultivated blueberry standard.

FIG. 6 is a graph and chart which depict an HPLC chromatogram at 280 nm of the total phenolics profile of a cultivated blueberry standard, and the characterization of phenolic compounds using RP-HPLC with UV detection.

FIG. 10 is a graph and chart which depict the proanthocyanin profile of Alaskan Blueberries and the proanthocyanidin content of Alaskan Blueberries, blueberry, cocoa, and cranberry.

DETAILED DESCRIPTION OF THE INVENTION

Definitions

Figure 1:
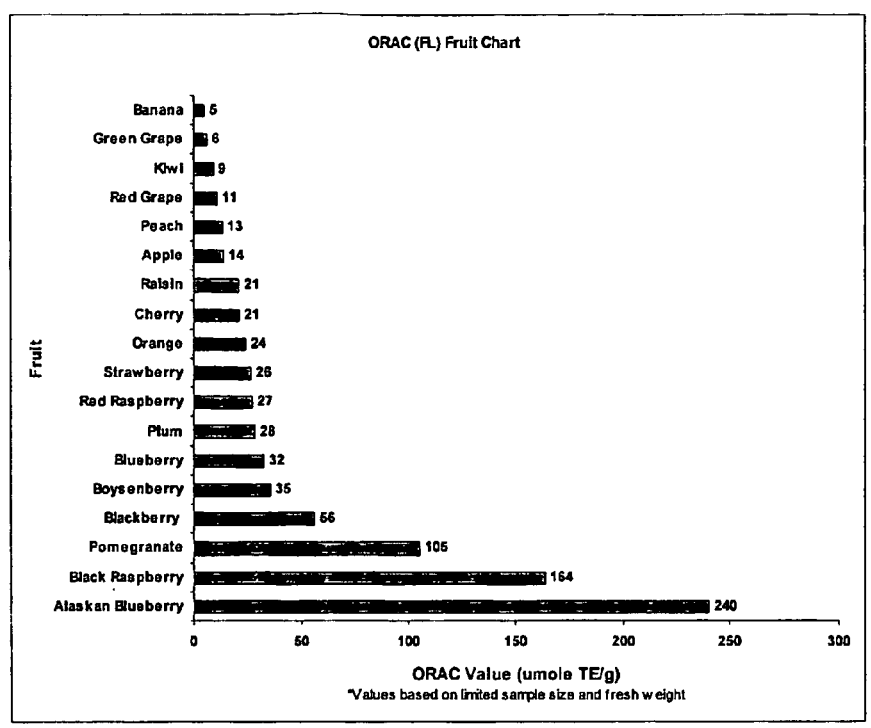
FIG. 1 is a chart which depicts Hydrophilic ORAC ranking of fruits.

"ORAC" refers to the Oxygen Radical Absorbing Capacity developed by the United States Department of Agriculture.

"TE" refers to Trolox Equivalents used in ORAC assays; Trolox is a water-soluble analog of Vitamin E.

"Anti-oxidant" refers to a chemical substance with the ability to scavenge oxygen "free radicals."

"Free Radical" refers to a compound having an unpaired electron, particularly an unpaired electron associated with an oxygen atom of the compound.

"Maturity" refers to the growth phase of *Vaccinium* species plants following fruit set, when organoleptic properties of fruit, for example, pigment, taste, and texture, are fully-developed and acceptable for human consumption as food.

"Peak ripeness" refers to the time in *Vaccinium* plant maturity when fruits have full, uniform coloring; are flavorful; and have begun to soften.

"High latitude" refers to a latitude which is at least about 55 degrees north or south of the equator of the Earth.

"Photoperiod" refers to a time of extended or continuous exposure to sunlight and, in particular, UV-B radiation.

"Freeze/thaw cycle" or "freeze cycle" refers to a period when berries are converted from fresh to frozen or from thawed to frozen again, either pre- or post-harvest.

"Phytochemicals" refers to naturally occurring chemical substances in plants, including phenylpropanoid pathway compounds, having biological activities.

"Refractance window drying" refers to a publicly disclosed drying method that uses a heat transfer process and specific properties of water to gently remove moisture while maintaining the maximum integrity of natural material(s) in the substance being dried.

"Milk derivative" refers to a substance derived from the milk of mammals, including, for example, cream, yogurt, cottage cheese, sour cream, soft and hard cheeses, butter and other dairy spreads, and the like. This term further refers to non-dairy substitutes for their dairy equivalents, such as margarine.

"Effecting" refers to the process of producing an effect on biological activity, function, health, or condition of an organism in which such biological activity, function, health, or condition is maintained, enhanced, diminished, or treated in a manner which is consistent with the general health and well-being of the organism.

"Enhancing" the biological activity, function, health, or condition of an organism refers to the process of augmenting, fortifying, strengthening, or improving.

"Physiologically acceptable carrier", refers, but is not limited to, pharmaceutically acceptable tablets, capsules, powders, solutions, dispersions, or liquids for oral administration. The subject compositions may be compounded with other physiologically acceptable materials which can be ingested, including, but not limited to, foods such as food bars, beverages, powders, cereals, cooked foods, food additives, and candies. Another ingestible form is a dietary supplement, such as a snack or wellness dietary supplement, which may be in oral formulation(s) such as tablets, capsules, powders, bars, solutions, dispersions, or liquids.

Vaccinium Species Compositions and Methods for Using Same

Compositions of the Inventive Subject Matter

The present invention relates to a composition comprising:
i. one or more berries, leaves, roots, and/or root barks obtained from one or more plant species of the genus *Vaccinium*, wherein said plant(s) is/are grown under the following conditions:
  (a) Subject to one or more uninterrupted photoperiod(s) of at least about 18 hours to 24 hours per day for about 60 days during flowering and fruit setting; and (b) Subject to one or more uninterrupted photoperiod(s) of at least about 15 hours per day for about 30 days during fruit ripening and maturity.

In another aspect of the inventive subject matter, said plant(s) is/are grown for at least about 7 days past peak fruit ripeness. Additional growth past peak ripeness permits additional production and concentration of beneficial substances in the plant(s).

The growing conditions of the inventive subject matter comprise growth of plant(s) at a latitude greater than 55 degrees north or south of the equator of the Earth. More preferably, in order to obtain the benefits described herein, the growing conditions comprise growth of said plant(s) at a latitude greater than 66 degrees north or south of the equator of the Earth.

In a preferred embodiment, growth conditions comprise the additional step of exposing said plant(s) to one or more freeze cycle(s) during growth and/or post-harvest. In this aspect of the inventive subject matter, processing the berries with a freezing step is expected to induce phenylpropanoid pathway enzymes and either stabilize or improve the ORAC values. Therefore, these factors are expected to make Plant(s) berries a previously unrecognized, preferred substance for an antioxidant nutraceutical supplement. A product formulated by this method would retain its preferred whole food composition and more lenient regulatory status.

In an alternate aspect of the inventive subject matter, the composition is produced by the additional step of drying said berries, leaves, roots, and/or root barks. More preferably, said drying step is a refractance window drying process.

A particular advantage of the inventive subject matter is that it does not require an independent processing, extraction, or concentration step, as is now required in the prior art to produce a physiologically significant quantity of beneficial substances. Thus, in a composition of the inventive subject matter, said dried berries, leaves, roots, and/or root barks do not require an additional processing or extraction step.

A composition of the inventive subject matter is produced from one or more plant species of the genus *Vaccinium*, selected from the group consisting of *V. alaskensis, V. axillare, V. caespitosum, V. caespitosum* var. *paludicola, V. membranaceum, V. parvifolium, V. ovalifolium, V. oxycoccus, V. shikokianum, V. uliginosum* subsp. *alpinum, V. uliginosum* var. *salicinum, V. uliginosum* subsp. *microphyllum, V. vitisidaea* subsp. *minus, V. vitis-idaea* subsp. *vitis-idaea*.

A composition of the inventive subject matter most preferably comprises the berries of said plant(s).

Further, as will be apparent to one of ordinary skill in the art, the growth conditions and processing steps of the inventive subject matter may readily be combined in various combinations, as described in the following aspects of the inventive subject matter:

In another aspect of the inventive subject matter, a nutraceutical would be prepared from berries having undergone at least one freeze-thaw cycle prior to harvest, cleaned of debris, pureed, and dehydrated by refractance window drying. The dried granular material is then milled into a fine powder for use in various dosage forms.

In another preferred embodiment, a nutraceutical would be prepared from berries not having undergone at least one freeze-thaw cycle prior to harvest, but would be cleaned of debris and frozen and thawed post-harvest for at least one cycle. Upon thaw, frozen berries would be pureed, and dehydrated by refractance window drying. The dried granular material is then milled into a fine powder for use in various dosage forms.

In another aspect of the inventive subject matter, a nutraceutical would be prepared from berries having undergone at least one freeze-thaw cycle prior to harvest, cleaned of debris and frozen and thawed at least once. Upon thaw, frozen berries would be pureed, and dehydrated by refractance window drying. The dried granular material is then milled into a fine powder for use in various dosage forms.

In another aspect of the inventive subject matter, phytopharmaceutical substances would be made from berries having undergone at least one freeze-thaw cycle prior to harvest or post-harvest and extracted with an appropriate solvent to concentrate specific types of substances from forms processed further as described above.

In another aspect of the inventive subject matter, phytopharmaceutical substances would be made from berries having undergone at least one freeze-thaw cycle prior to harvest or post-harvest and extracted with an appropriate solvent to concentrate specific types of substances from forms not processed further as described above.

In another aspect of the inventive subject matter, phytopharmaceutical substances would be made from berries not having undergone at least one freeze-thaw cycle prior to harvest or fresh, post-harvest and extracted with an appropriate solvent to concentrate specific types of substances from forms further processed as described above.

In another aspect of the inventive subject matter, phytopharmaceutical substances would be made from berries not having undergone at least one freeze-thaw cycle prior to harvest or fresh, post-harvest and extracted with an appropriate solvent to concentrate specific types of substances from forms not processed as described above.

In another aspect of the inventive subject matter, pharmaceutical substances would be made from fresh berries or berries having undergone at least one freeze-thaw cycle prior to harvest or post-harvest and extracted with an appropriate solvent to concentrate specific types of substances from processed or unprocessed forms as described above.

In another aspect of the inventive subject matter, aerial parts, for example leaves, stem, and stem bark, may be an additional component of nutraceuticals from processed or unprocessed forms of berries as described above.

In another aspect of the inventive subject matter, roots and root bark may be an additional component of the types of nutraceuticals from processed or unprocessed forms of berries as described above.

In another aspect of the inventive subject matter, phytopharmaceuticals would be made from aerial parts, flowers, leaves, stem and stem bark, or root and root bark extracted with an appropriate solvent to concentrate specific types of substances from *Vaccinium* species with characteristics as described above.

In another aspect of the inventive subject matter, pharmaceuticals would be made from aerial parts, flowers, leaves, stem and stem bark, or root and root bark extracted with an appropriate solvent to concentrate specific types of substances from *Vaccinium* species with characteristics as described above.

Plants of the Genus *Vaccinium*. There are approximately 90, of approximately 400 species of *Vaccinium*, that are distributed widely across the Northern Mediterranean, Southern Europe, Central Europe, Northern Europe, North Asia, South Asia, Central Asia, and East Asia. This includes approximately 50 species native to North America. Essentially wherever humans migrated, to bogs, damp forests, whether temperate or subtropical, broadleaf or conifer, there were blueberries of varying degrees of edibility, productivity, and population density. *Vaccinium* is a genus with a very long association with the part of the human race that radiated out of Africa and across Beringia. The berries of the inventive subject matter are selected from high latitude species of the genus *Vaccinium* found in Alaska and neighboring territories.

The *Vaccinium* genus is taxonomically complex. Hybridization and polyploidy make delineation of species notoriously difficult. For example, dwarf bilberry, *V. myrtillus*, is believed to have received genetic material from globe huckleberry, *V. globulare*, blue huckleberry, *V. membranaceum*, and/or dwarf huckleberry, *V. caespitosum*. Conversely, some taxonomists believe that the blue huckleberry may be a derivative of globe huckleberry and dwarf bilberry. Naturally occurring dwarf bilberry-lingonberry, *V. vitis-idaea*, hybrids have been reported in parts of northern Europe. Numerous intermediate forms have been observed, although fruit set is apparently rare in these hybrid populations. *V. X intermedium* is a natural hybrid resulting from a dwarf bilberry-lingonberry cross.

Subspecies and varieties of some of the species occurring in Alaska and neighboring territories have northern circumpolar ranges, and include *V. oxycoccus, V. uliginosum*, and *V. vitis-idaea*. Interestingly, the most common *Vaccinium* species, *V. myrtillus*, is not found in Alaska. *Vaccinium* species occurring in Alaska and likely at the border of neighboring territories that are not typical species of commerce are described in Table 1.

TABLE 1

*Vaccinium* species of Alaska and neighboring territories.

| Species Name | Location |
| --- | --- |
| *V. alaskensis* | SC, SE |
| *V. axillare* | Japan, (A)* |
| *V. caespitosum* | SC, SE, Canada |
| *V. caespitosum* var. *paludicola* | SC* |
| *V. membranaceum* | Canada, (SE)* |
| *V. parvifolium* | SE, Canada |
| *V. ovalifolium* | A, SC, SE, SW |
| *V. oxycoccus* | Ubiquitous |
| *V. shikokianum* | Japan, (A)* |
| *V. uliginosum* subsp. *alpinum* | Throughout AK |
| *V. uliginosum* var. *salicinum* | Scattered |
| *V. uliginosum* subsp. *microphyllum* | A, FN, SC |
| *V. vitis-idaea* subsp. *minus* | Throughout AK |
| *V. vitis-idaea* subsp. *vitis-idaea* | Kamchatka, (A)* |

A = Aleutians;
(A)* = predicted in the western Aleutians;
AK = Alaska;
FN = Far North Alaska;
SC = Southcentral Alaska;
SC* = Southcentral, specifically Prince William Sound;
SE = Southeast Alaska;
(SE)* = predicted in Southeast Alaska;
SW = Southwest Alaska.

The Phenylpropanoid Pathway. Plants produce a distinct group of secondary metabolites collectively named flavonoids. The pathway that leads to flavonoid synthesis is a branch of the general phenylpropanoid pathway that exists in all higher plants. Genes encoding enzymes of this pathway are developmentally and tissue-specifically regulated and are expected to be induced by environmental stresses such as nutrient deficiency, drought, prolonged cold, exposure to intense UV light, and pathogen attack. The flavonoids, which are the best defined group of polyphenols in the human diet, themselves comprise a large and complex group, all of which contain a three-ring structure with two aromatic centers and a central oxygenated heterocycle.

Important metabolites of the phenylpropanoid pathway are isoflavones such as quercetin, myrtillin, daidzein, and genistein; flavanols, such as catechin and epicatechin; pterocarpans such as medicarpin and glyceollins; anthocyanins and anthocyanosides such as cyanidin, delphinidin, malvidin, petunidin, and peonidin; proanthocyanidins or tannins, and lignin. The isoflavonoids are essential for different types of plant-microbe interactions, and are also important chemoattractants and signal molecules for symbiotic bacteria. Different isoflavonoids are also either precursors to, or are themselves the major phytoalexins in plants, which play key roles in non-specific plant defense against bacterial and fungal pathogens. The activation of isoflavonoid synthesis during the disease resistance response is important for providing these many defense compounds. As a major part of their role as defense compounds against stress and disease, most of the phenylpropanoid pathway metabolites protect plants against oxidative stress.

Antioxidants. Oxidative stress is defined as an imbalance between oxidants and antioxidants in favor of the former, resulting in oxidative damage to molecules such as DNA, lipids and proteins. After life-long free-radical insult on an organ which already shows increased vulnerability to OS, functional deficits are observed. Since its introduction almost 50 years ago, the free radical hypothesis of aging has become popular to explain age-related changes that result from an increasing inability to cope with oxidative stress that occurs throughout the life-span from aerobic metabolism and is associated with increasing sensitivity to the effects of oxidative stressors.

"Free Radicals" are characterized by an unpaired electron associated with an oxygen atom of a compound. They are very unstable and quickly react with other compounds. In biological systems, common radicals produced include the peroxyl radical, which is the most common radical in biological systems; the hydroxyl radical; the superoxide radical, which is produced by phagocytic cells and is beneficial in inactivating viruses and bacteria; the nitric oxide radical, which has some beneficial effects as a vasodilator and a neurotransmitter; the peroxynitrite anion, which is produced by the reaction of nitric oxide with superoxide; and hydrogen peroxide, which is not technically a free radical, but is formed from reactions of free radicals and can also cause damaging oxidative events in cells. In humans, free radicals are produced by metabolic processes, cigarette smoke, photochemical smog, pesticides, and drugs, among others.

Conversely, an antioxidant is any substance that, when present at low concentrations compared to those of an oxidizable substrate, significantly delays or prevents the oxidation of such substrate, by "absorbing" the unpaired electron. The normal antioxidant defense systems in biological organisms are both enzymatic and nonenzymatic. Although both are important in biological systems, foods furnish nonenzymatic antioxidants such as α-tocopherol, ascorbic acid, glutathione, flavonoids, β-carotene, uric acid, and proteins such as albumin, ceruloplasmin, transferrin, and metallothionein.

Researchers have analyzed ORAC of commercial blueberry varieties and less common species from the United States and Canada, and compared them to the closely related bilberry from Germany. Highbush blueberry, *V. corymbosum*, and lowbush blueberry, *V. angustifolium*, are the primary species of blueberries used by the food industry in the United States. In recent days, the USDA asserts that consumption of one-half cup, 72.5 g, of blueberries per day increases ORAC intake by 1-3.2 mmol, depending upon the blueberry variety and maturity, making a small but beneficial contribution to a healthy diet for normal individuals.

The antioxidant capacity of blueberries varies considerably because of the wide range of reported anthocyanin concentrations. Bilyk and Sapers (1986) found that four varieties of cultivated highbush blueberry had total anthocyanin concentrations that varied by about 15%. Highbush blueberries have been reported to have an anthocyanin content of 25-495 mg/100 g fresh weight. Gao and Mazza (1994) reported, using HPLC techniques to measure anthocyanins, that most highbush blueberry samples contained about 100 mg anthocyanins/100 g and lowbush blueberry cultivars contained 150-200 mg anthocyanins/100 g. Others report that lowbush blueberries, grown in Maine and Eastern Canada, have about 138 mg anthocyanins per 100 g. Rabbiteye blueberries, *V. ashei*, grown in the southern U.S., have an anthocyanin content in the range of 62 mg/100 g to 210-272 mg/100 g. In contrast, bilberry has been reported to have the highest anthocyanin content of 300-698 mg anthocyanin/100 g.

According to studies performed by Prior and colleagues, the total antioxidant capacity, measured as ORAC, ranged from a low of 13.9 to 44.6 mmol TE/g fresh berries in the acetonitrile extracts of the different cultivars of blueberries. The overall mean of all commercially available cultivars was 24.0+/−2.0. Certain highbush varieties and late harvest rabbiteye cultivars had ORAC values (i.e. 32.4, 37.1, 42.3, 37.8, and 34.3 TE/g, respectively) that approached the value observed for the bilberry (44.6 TE/g). It has been suggested that region does not affect the antioxidant score, based on analyses by the USDA Human Nutrition Research Center on Aging at Tufts University (Boston, Mass.) of berries from the northern highbush variety, Jersey, grown in Oregon, Michigan and New Jersey.

There appears, however, to be two clusters of ORAC values in the lowbush blueberries. The first included lowbush from Prince Edward Island and Nova Scotia, and Fundy lowbush blueberries which are relatively high in ORAC (mean: 41.8 TE/g), anthocyanins, and total phenolics. The second cluster included lowbush from Maine, and lowbush blueberries from other locations which are lower in ORAC (mean: 27.5 TE/g). At this time, the source of this variation, whether genetics, location, maturity or other factors, is not clear. Anthocyanins in the lowbush blueberries are not as high as the bilberry relative to ORAC values as reflected in the ratio of anthocyanins to ORAC, 0.37 TE/g versus 0.57 TE/g. Further, the results of Prior et al. in general seem to be a little lower than some of the other reports; however, the particular anthocyanin compound used as a standard and its associated molar absorption coefficient can influence the absolute amounts calculated.

Maturity at harvest had a marked effect on ORAC, total anthocyanins and total phenolics of the berries, as demonstrated for the cultivars of rabbiteye blueberries. Berries harvested immediately after turning blue had lower ORAC and total anthocyanins than well-matured berries that were harvested 49 days later. ORAC and total anthocyanins increased 224% and 261% respectively, in one cultivar, while they increased in the other cultivar by 164% and 176% respectively, with increasing maturity. Total phenolics increased by 169% and 113% in these cultivars, with increased maturity.

Ascorbate concentrations (1.3-16.4 mg/100 g) showed a significant variability between cultivars and species, but are typically less than or equal to 10% of the total ORAC. Although most of the samples had an ascorbate concentration between 9-16 mg/100 g, no consistent pattern emerged relative to ORAC, anthocyanins or total phenolics. Using an ORAC value for ascorbate of 5.6 mmol TE/g, it was calculated that the antioxidant capacity contributed by ascorbate to the total antioxidant capacity, measured as ORAC, was 2.3% for the highbush and rabbiteye berries. Ascorbate in lowbush berries contributed only 1.5% while in the bilberry sample, the contribution of ascorbate to ORAC was only 0.2%. Thus, it is clear that ascorbate does not make a major contribution to the antioxidant capacity of any of the blueberries sampled.

Advantages of the Inventive subject matter. On a fresh weight basis, Alaskan *Vaccinium* species have the highest antioxidant capacity of all *Vaccinium* berries tested to date, including European bilberry. For a comparison of the ORAC value of the berries of the inventive subject matter to others, see FIG. 1. Expressed in a different way, on a mmol/g basis, for peroxyl radical in hydrophilic and hydrophobic conditions, as well as for hydroxyl and peroxynitrite radicals, see FIG. 2 and FIG. 3?). This is unprecedented according to Wang and Jiao (2000), who found unique patterns of oxygen radical scavenging ability in different berry genera. Overall, fruit juice from different cultivars of 'Hull Thornless' blackberry, 'Earliglow' strawberry, 'Early Black' cranberry, 'Jewel' raspberry, and 'Elliot' blueberry had the highest antioxidant capacity against superoxide radicals, peroxyl, hydroxyl radicals, and singlet oxygen. Blackberries had the highest antioxidant capacity inhibition of superoxide, peroxyl, and hydroxyl radical. Strawberry was second best in the antioxidant capacity assay for these same free radicals. With regard to singlet oxygen scavenging activity, strawberry had the highest value, while blackberry was second. Cranberries had the lowest inhibition of peroxyl activity. Meanwhile, blueberries had the lowest antioxidant capacity against hydroxyl and singlet oxygen, in direct contrast to the results of hydroxyl radical scavenging by Alaska *Vaccinium*.

Further, in the Alaskan *Vaccinium* preparation, total anthocyanin concentration is 37.43 mg/g and total phenolic content is 69.63 mg/g on a dry weight basis. The value for bilberry, on a fresh weight basis, is cited in the literature as the highest, at 300-698 mg anthocyanin/100 g, depending upon the anthocyanin reference compound used for comparison, and 525 mg/100 g total phenolics. Prior et al., utilizing cyanidin 3-glucoside as a standard, found the average bilberry anthocyanin concentration to be 299.5 mg/100 g fresh weight. Compared to the same standard, the anthocyanin concentration of Alaska *Vaccinium* is estimated to be 312-333 mg/100 g fresh weight, and the total phenolics are 580-619 mg/100 g fresh weight.

The ORAC values observed are, across the board with various radicals, and the correlation to anthocyanin, proanthocyanidin, and phenolic content are unprecedented and were not predicted. The bilberry has always dominated such comparisons and, based on those, regulatory agencies such as the German Commission E regard any other *Vaccinium* source as a possible adulterant to *V. myrtillus* preparations.

Although most researchers would argue that *Vaccinium* is selective about its growing conditions, and that these influence antioxidant concentrations in unknown ways, Applicant expected a link between growing conditions and antioxidant content of Alaskan *Vaccinium* berries. Without being bound by any particular theory of mechanism of action, Applicant believes that the metabolites producing the observed ORAC, anthocyanin, proanthocyanidin, and phenolic content are generated by one or more stress-related phenylpropanoid pathway(s). At the very high latitudes where berries grow in Alaska, the photoperiod is greater than 17.5 hours at 55 degrees north and is continuous at 66 degrees north for approximately 3 months. Applicant believes that UV-B is strongest at low latitudes and high altitudes, that the ultraviolet bombardment at such latitudes produces the surprising results found, and expects that lower latitude plants do not produce such results because of the presence of a significant daily dark period. At higher latitudes, the sun is always low in the sky so that it takes a longer path through the atmosphere and more of the UV-B is absorbed. As unexpectedly discovered by Applicant, high latitude plants, exemplified by Alaskan plants, must synthesize a great deal of antioxidants to protect DNA, proteins, and lipids from free radical damage. Further, Applicant expects that the widely documented and publicized ozone-depletion at high latitudes makes exposure to UV-B even more intense than previously believed.

Applicant expects that the novel characteristics of high latitude berries, exemplified by Alaskan berries, results in part from the relatively low levels of annual precipitation in the Far North region of 4.8 inches, and in the Interior region of 10.8 inches, would enhance the phenylpropanoid pathway metabolites of the berries. In the Southcentral and Southeast regions, precipitation is 15.9 inches, and 54.38 inches, respectively, that are expected to actually enhance UV-B exposure due to prolonged cloud cover.

Further, Applicant expects that the novel characteristics of high latitude berries, exemplified by Alaskan berries, results in part because during the maturation phase of the berries in late July-early September, depending upon region, large temperature swings occurring during the increasing daily dark cycle further induce the phenylpropanoid pathway and corresponding production of antioxidant, anthocyanin, proanthocyanidin, and phenolic compounds.

Figure 3:
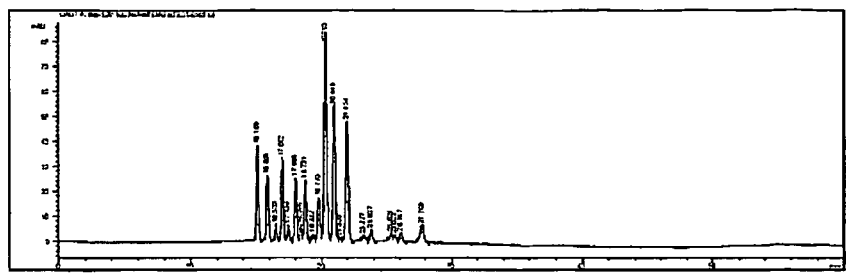
FIG. 3 is a graph which depicts separation of 10 common anthocyanins using RP-HPLC with UV detection for Alaskan berries.

Comparing the anthocyanin profiles of Alaskan berries found in FIG. 3 with a cultivated blueberry standard in FIG. 4. The magnitude of the detector response on the y-axis fingerprint of the Alaska berry profile is on dehydrated material, not concentrated extract as from standard berries, and is still significantly greater. The concentration of anthocyanins made development of a new gradient system necessary to affect separation, thereby causing different retention times of the compounds.

Figure 5:
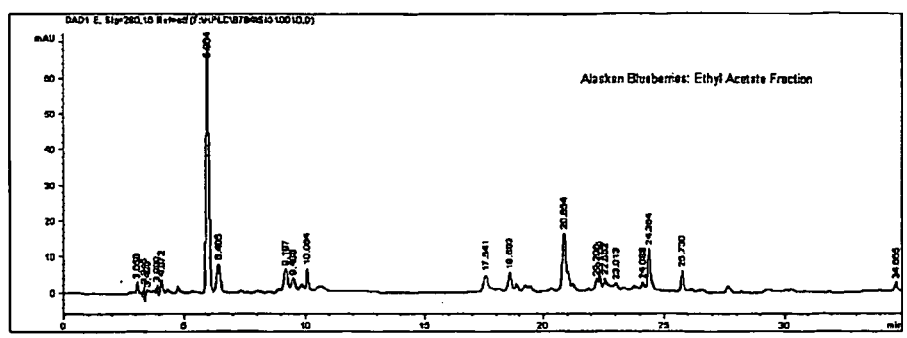
FIG. 5 is a graph which depicts an HPLC chromatogram at 280 nm of the total phenolics profile of wild Alaskan Blueberries.

Comparing the total phenolic profiles of Alaskan berries in FIG. 5 to a cultivated blueberry standard in FIG. 6. The magnitude of the detector response on the y-axis differs because the fingerprint of standard berries was from a concentrated extract and the Alaska berry profile is on the dehydrated material that was not extracted. Note the difference in retention times of the compounds.

Figure 7:
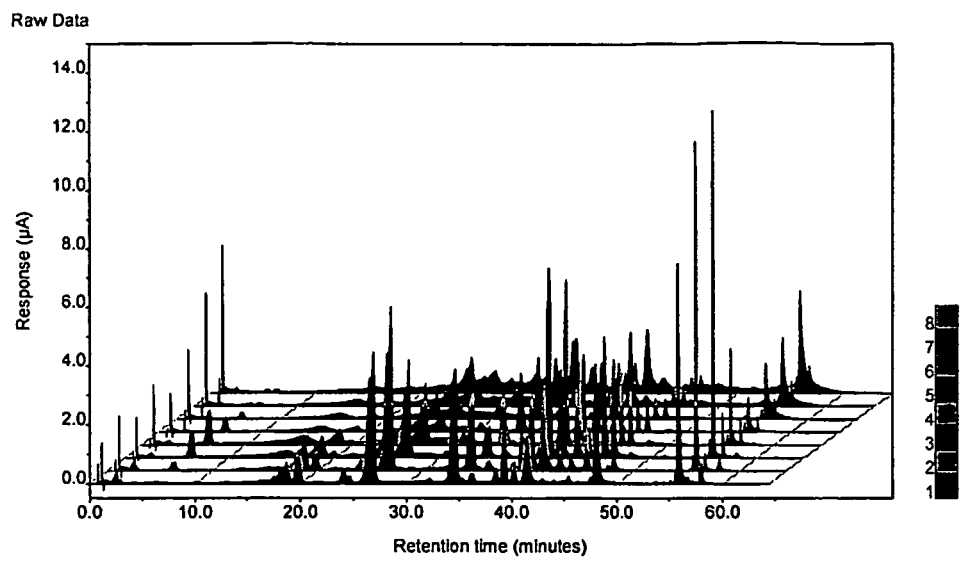
FIG. 7 is a chart which depicts the antioxidant fingerprint obtained by multi-channel ECD Detector for wild Alaskan Blueberries.
Figure 8:
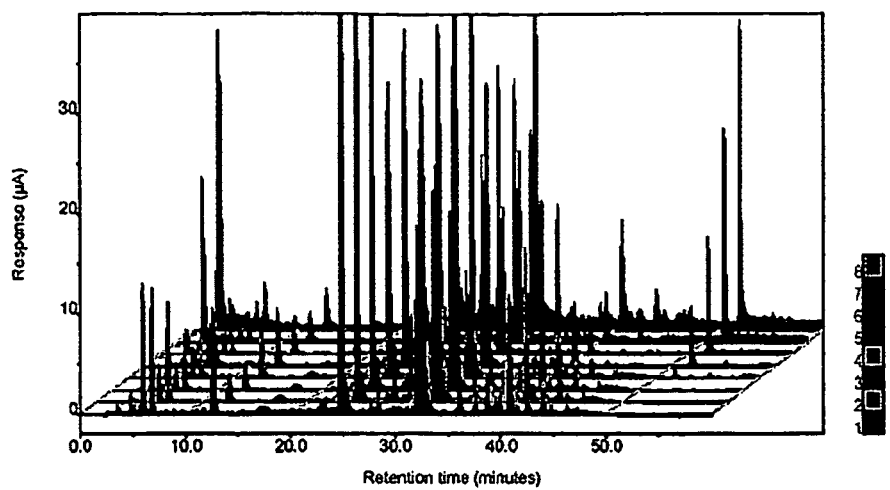
FIG. 8 is a chart which depicts antioxidant fingerprint obtained by the ESA 8-channel electron chemical detector for a cultivated blueberry standard.
Figure 9:
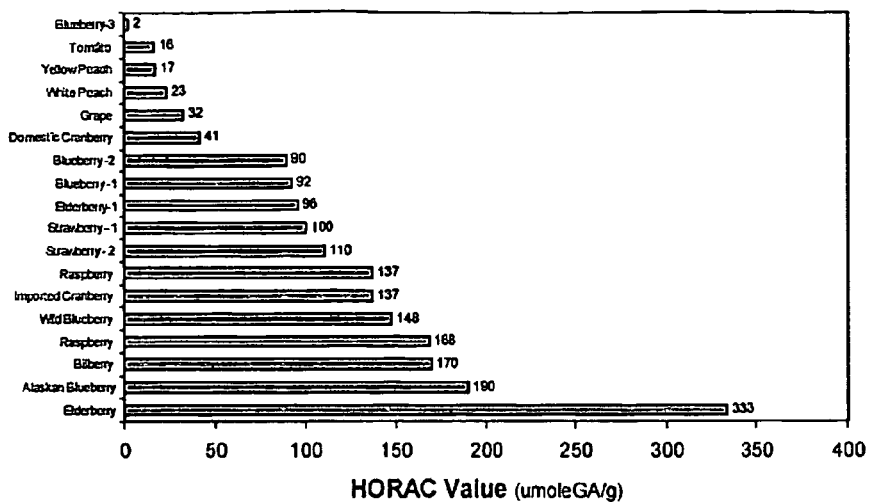
FIG. 9 is a chart which depicts the rank of antioxidant activity against hydroxyl radicals of fruits.
Figure 11:
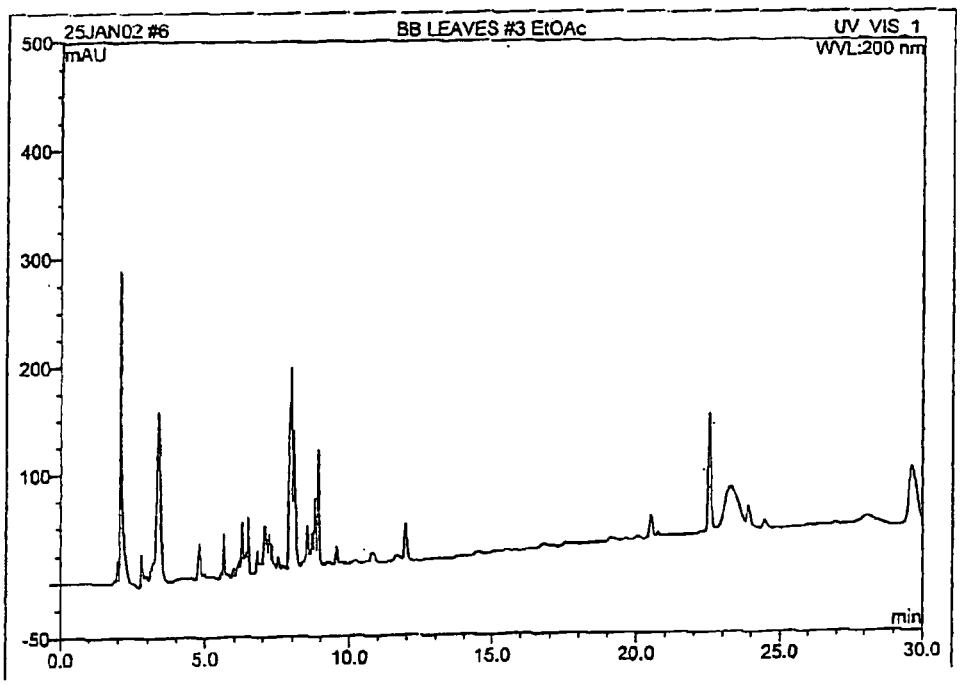
FIG. 11 is a graph which depicts an HPLC chromatogram at 200 nm of the total phenolics profile of wild Alaskan Blueberry leaves in ethyl acetate.
Figure 12:
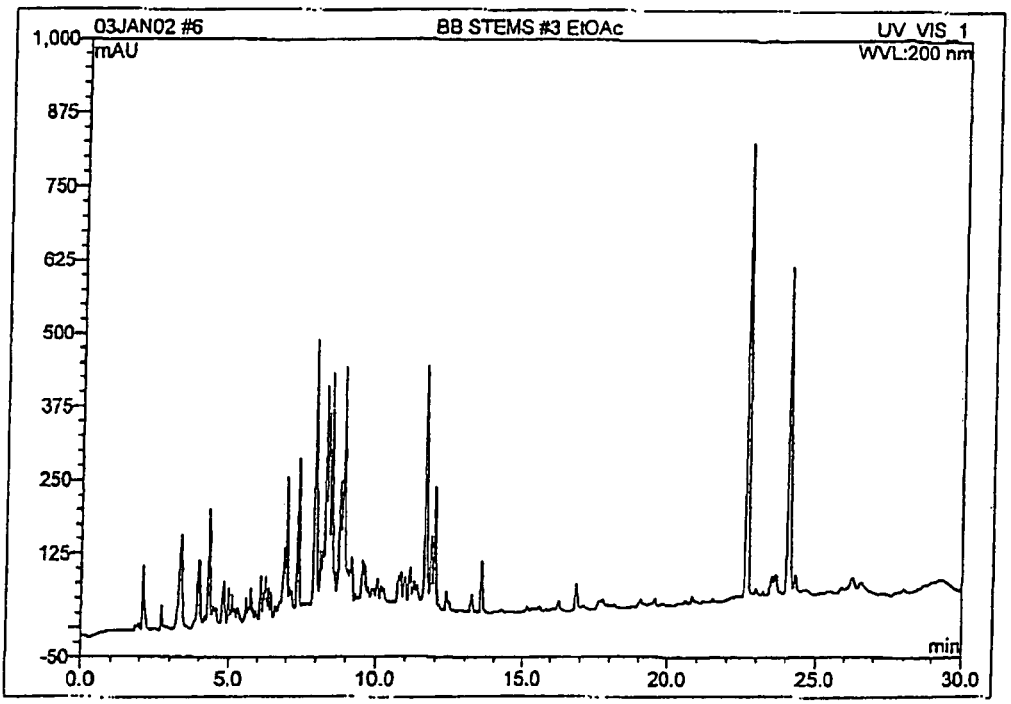
FIG. 12 is a graph which depicts an HPLC chromatogram at 200 nm of the total phenolics profile of wild Alaskan Blueberry stems in ethyl acetate.
Figure 13:
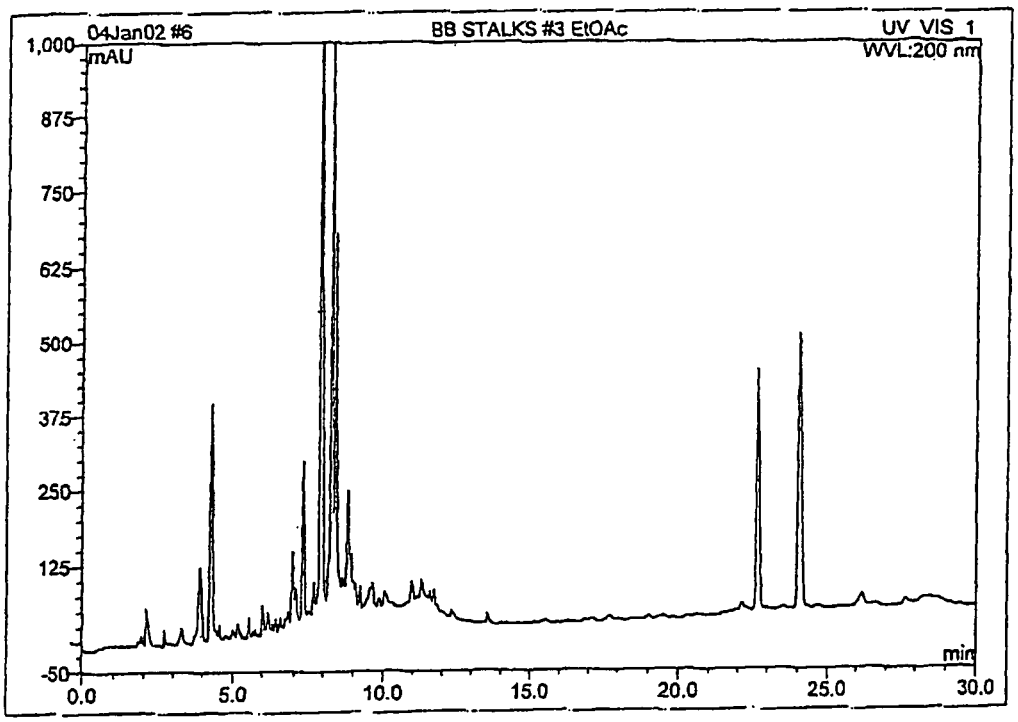
FIG. 13 is a graph which depicts an HPLC chromatogram at 200 nm of the total phenolics profile of wild Alaskan Blueberry stalks in ethyl acetate.
Figure 14:
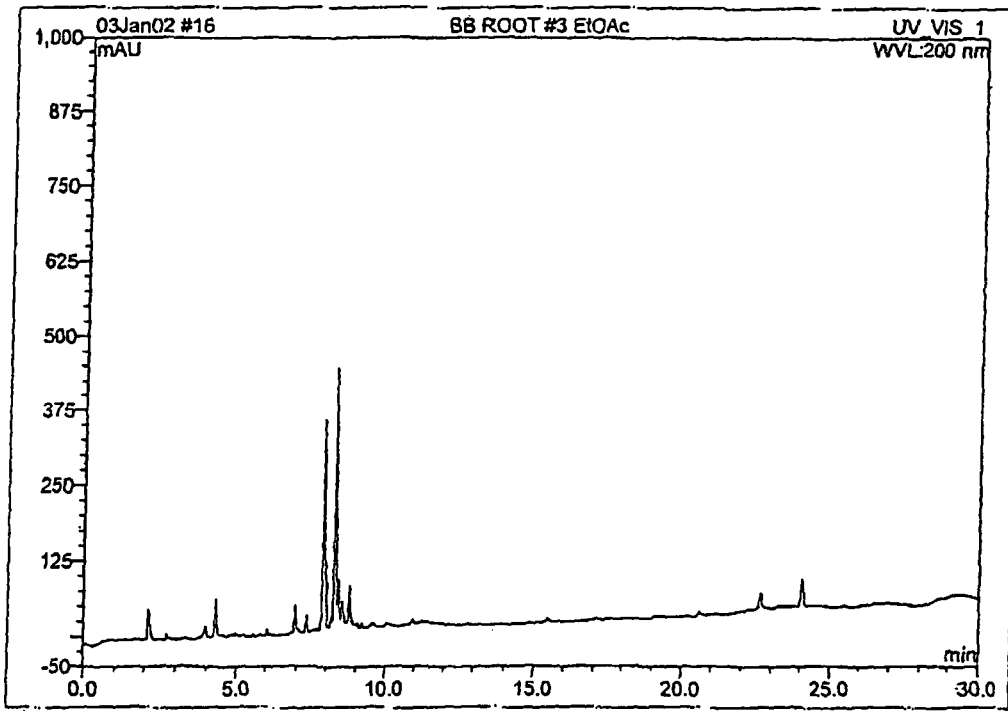
FIG. 14 is a graph which depicts an HPLC chromatogram at 200 nm of the total phenolics profile of wild Alaskan Blueberry root in ethyl acetate.
Figure 15:
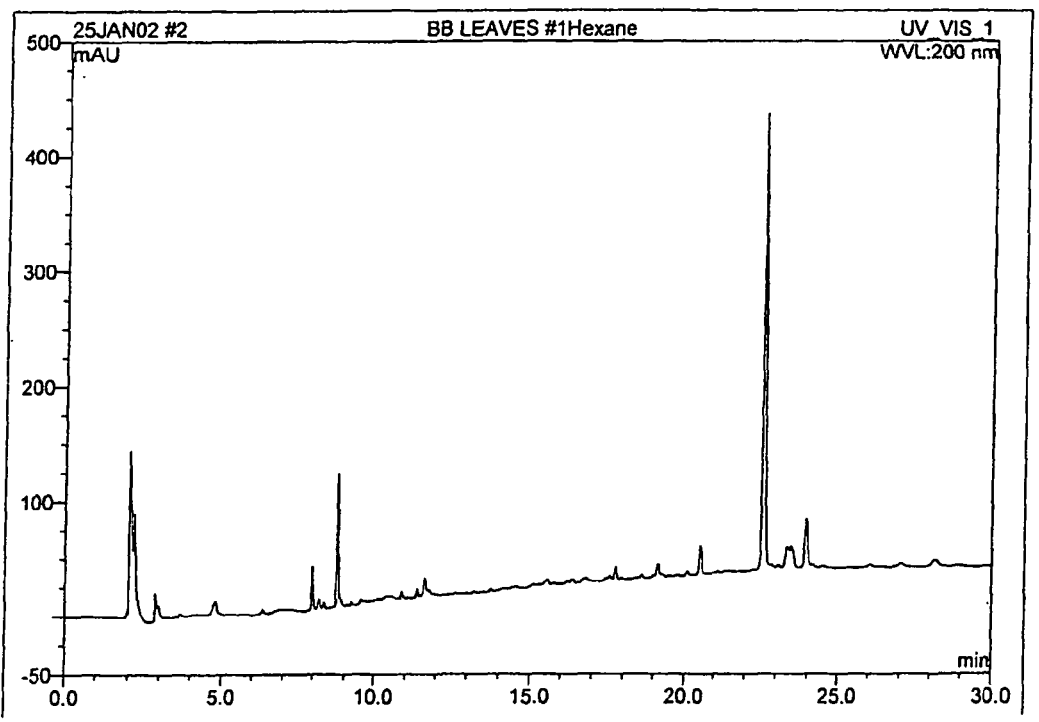
FIG. 15 is a graph which depicts an HPLC chromatogram at 200 nm of the total phenolics profile of wild Alaskan Blueberry leaves in hexane.
Figure 16:
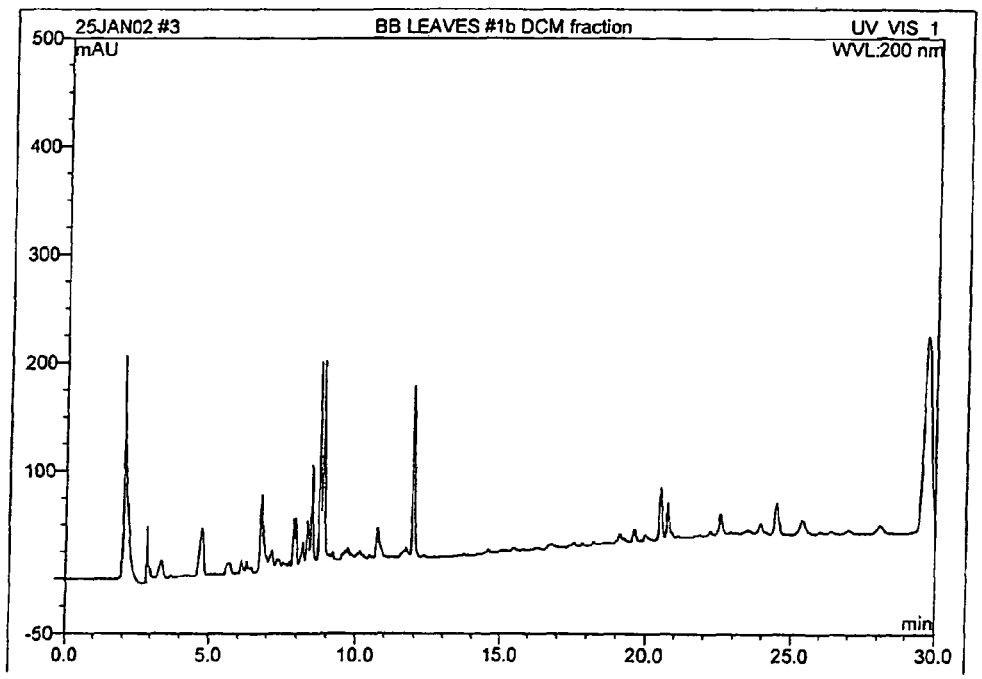
FIG. 16 is a graph which depicts an HPLC chromatogram at 200 nm of the total phenolics profile of wild Alaskan Blueberry leaves in dichloromethane.
Figure 17:
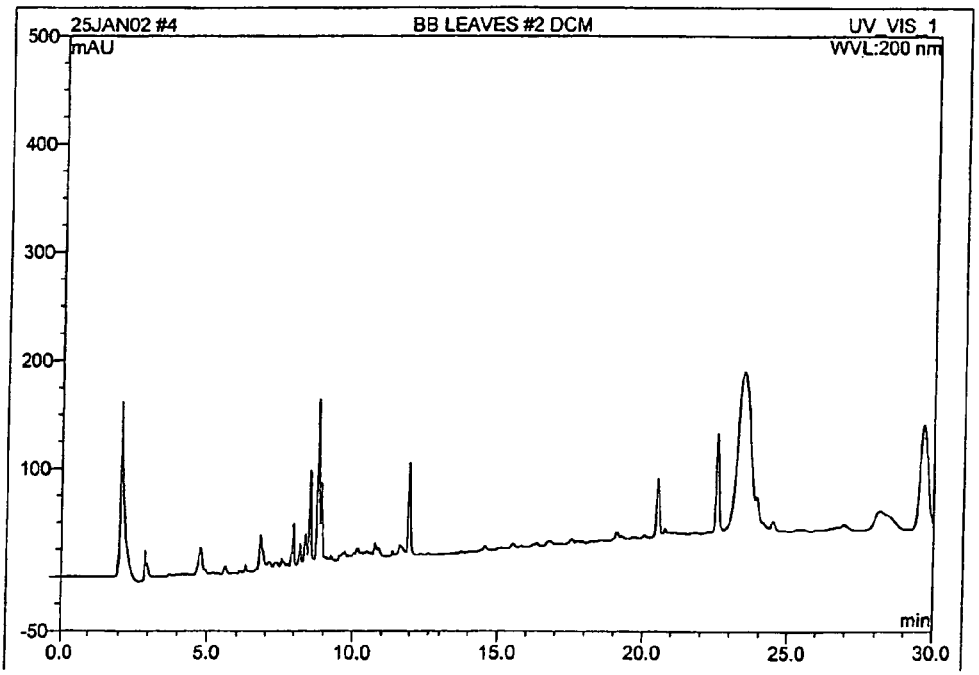
FIG. 17 is a graph which depicts an HPLC chromatogram at 200 nm of the total phenolics profile of wild Alaskan Blueberry leaves in dichloromethane.
Figure 18:
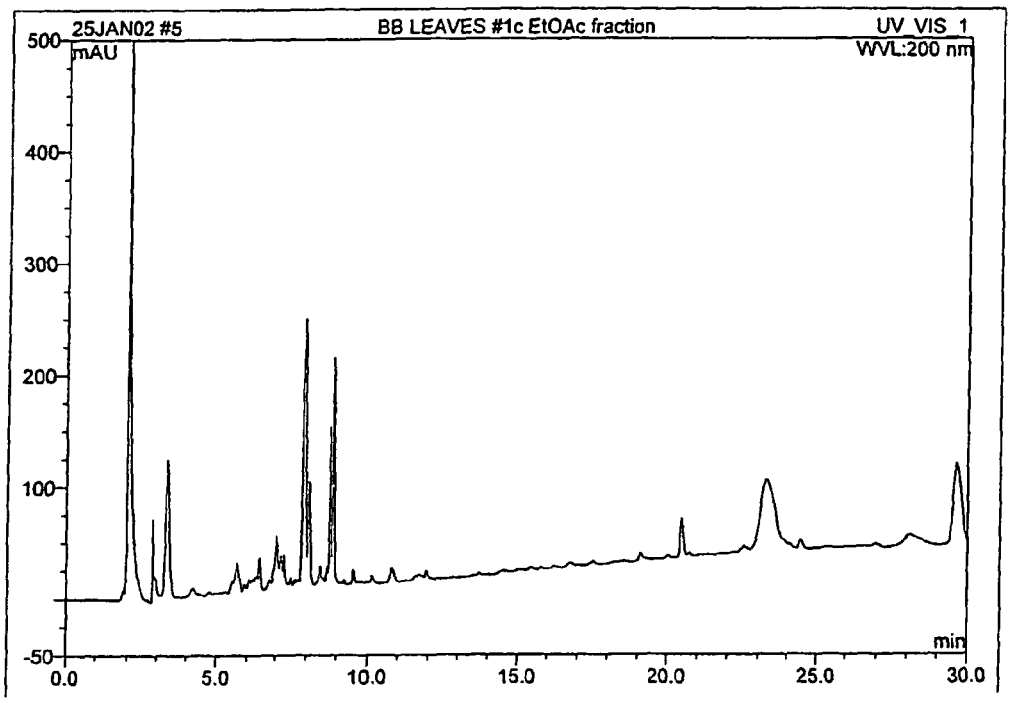
FIG. 18 is a graph which depicts an HPLC chromatogram at 200 nm of the total phenolics profile of wild Alaskan Blueberry leaves in ethyl acetate.
Figure 19:
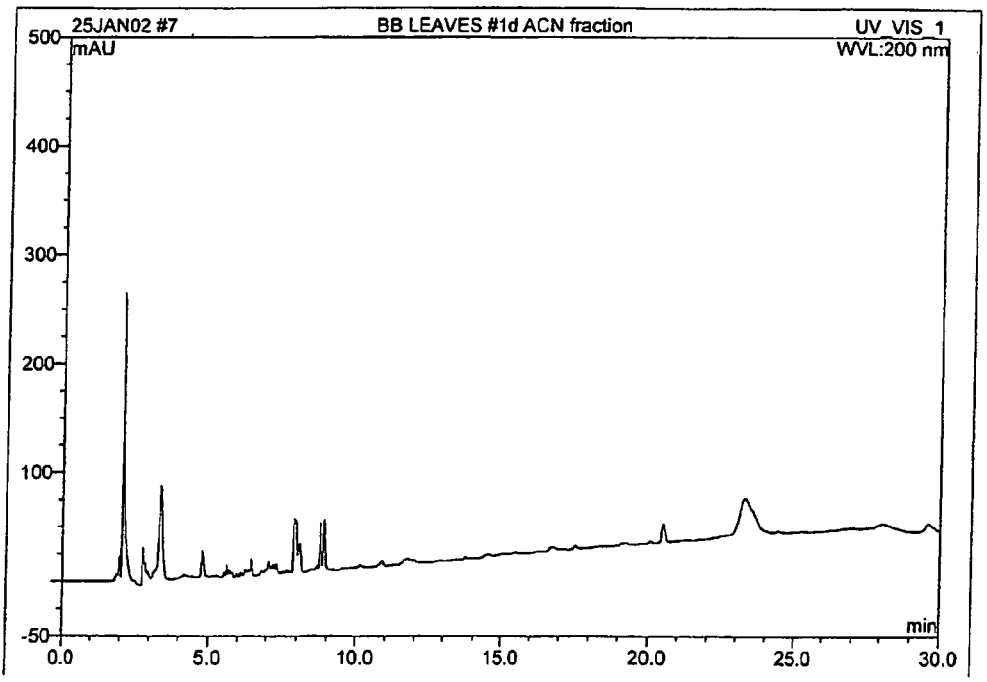
FIG. 19 is a graph which depicts an HPLC chromatogram at 200 nm of the total phenolics profile of wild Alaskan Blueberry leaves in acetonitrile.
Figure 20:
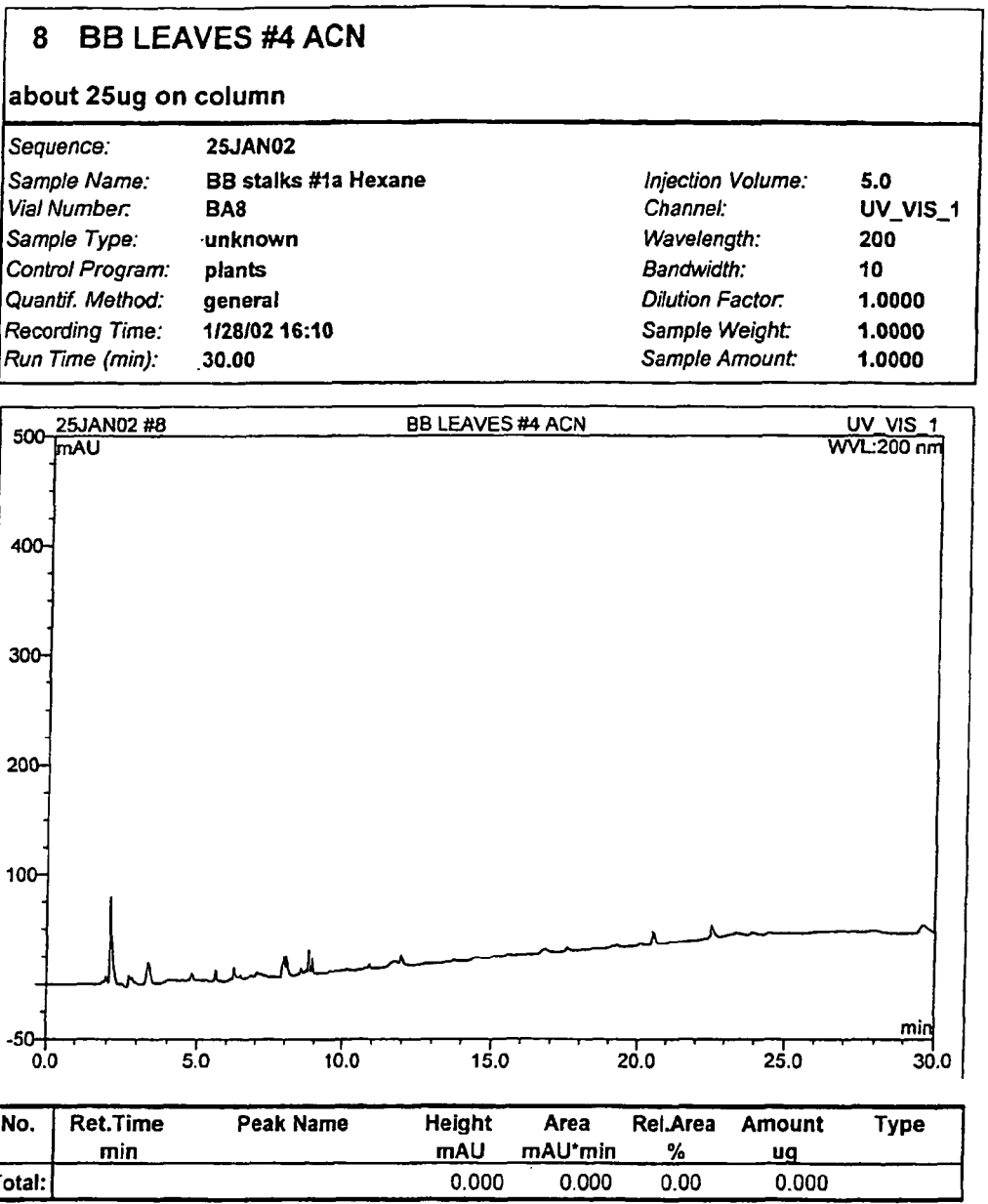
FIG. 20 is a graph which depicts an HPLC chromatogram at 200 nm of the total phenolics profile of wild Alaskan Blueberry leaves in acetonitrile.
Figure 21:
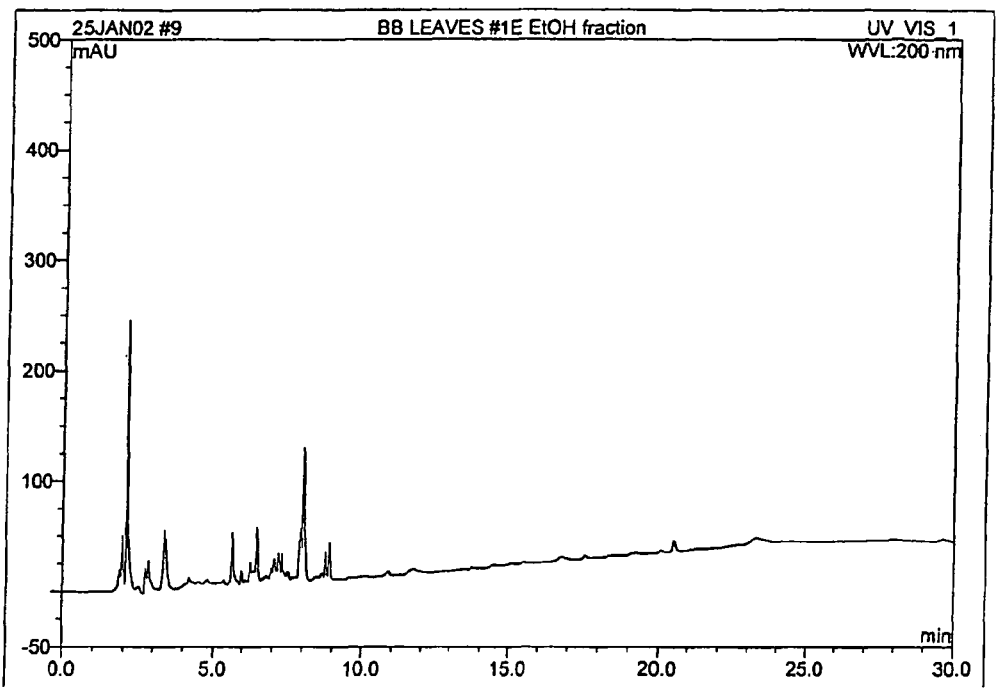
FIG. 21 is a graph which depicts an HPLC chromatogram at 200 nm of the total phenolics profile of wild Alaskan Blueberry leaves in ethanol.
Figure 22:
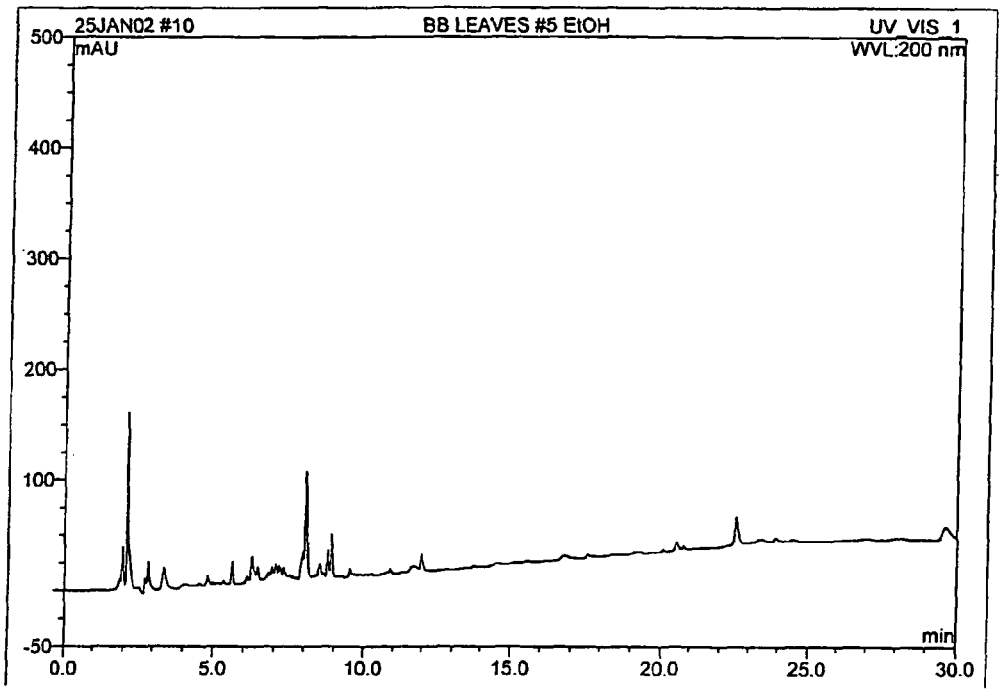
FIG. 22 is a graph which depicts an HPLC chromatogram at 200 nm of the total phenolics profile of wild Alaskan Blueberry leaves in ethanol.
Figure 23:
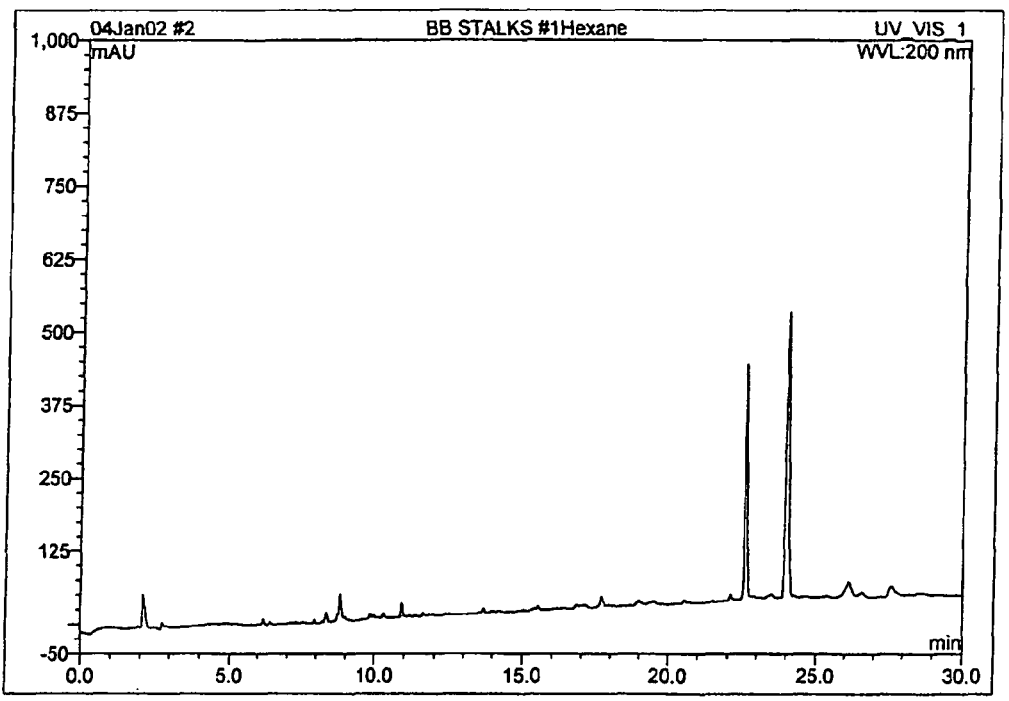
FIG. 23 is a graph which depicts an HPLC chromatogram at 200 nm of the total phenolics profile of wild Alaskan Blueberry stalks in hexane.
Figure 24:
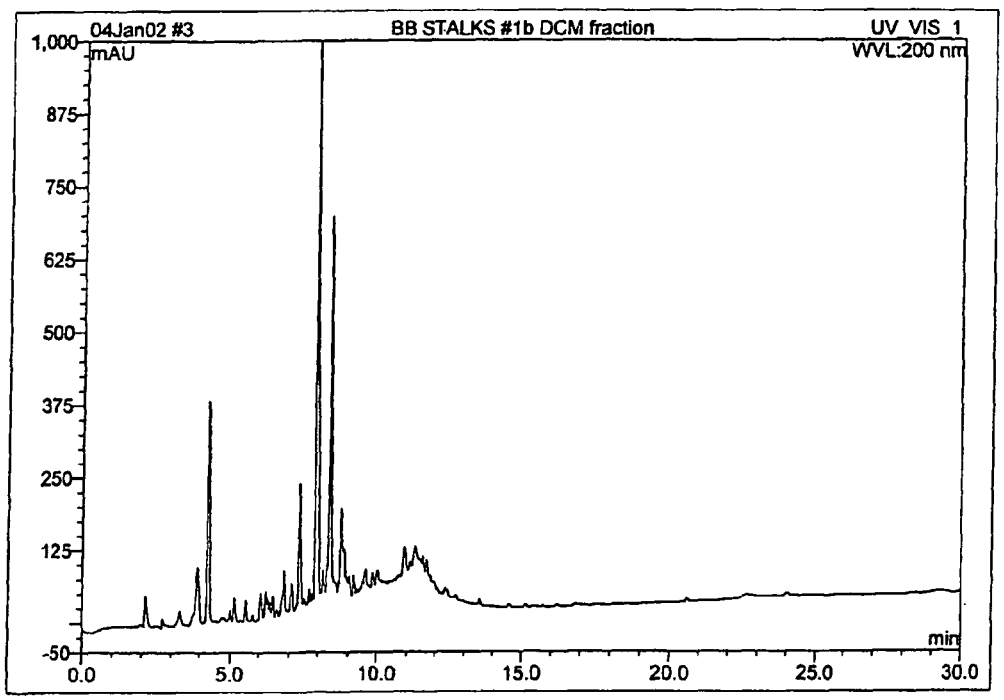
FIG. 24 is a graph which depicts an HPLC chromatogram at 200 nm of the total phenolics profile of wild Alaskan Blueberry stalks in dichloromethane.
Figure 25:
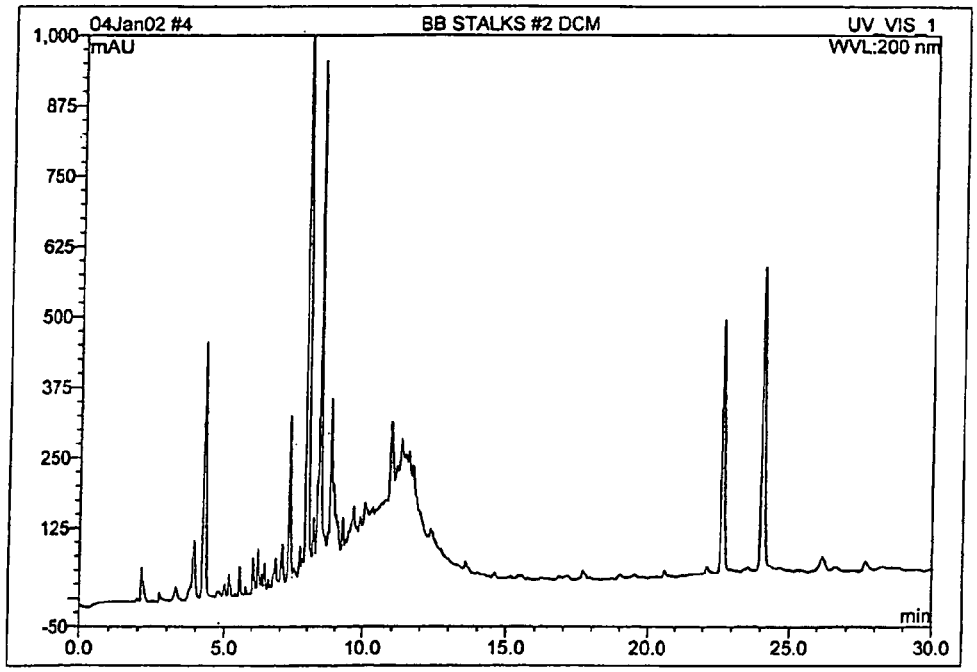
FIG. 25 is a graph which depicts an HPLC chromatogram at 200 nm of the total phenolics profile of wild Alaskan Blueberry stalks in dichloromethane.
Figure 26:
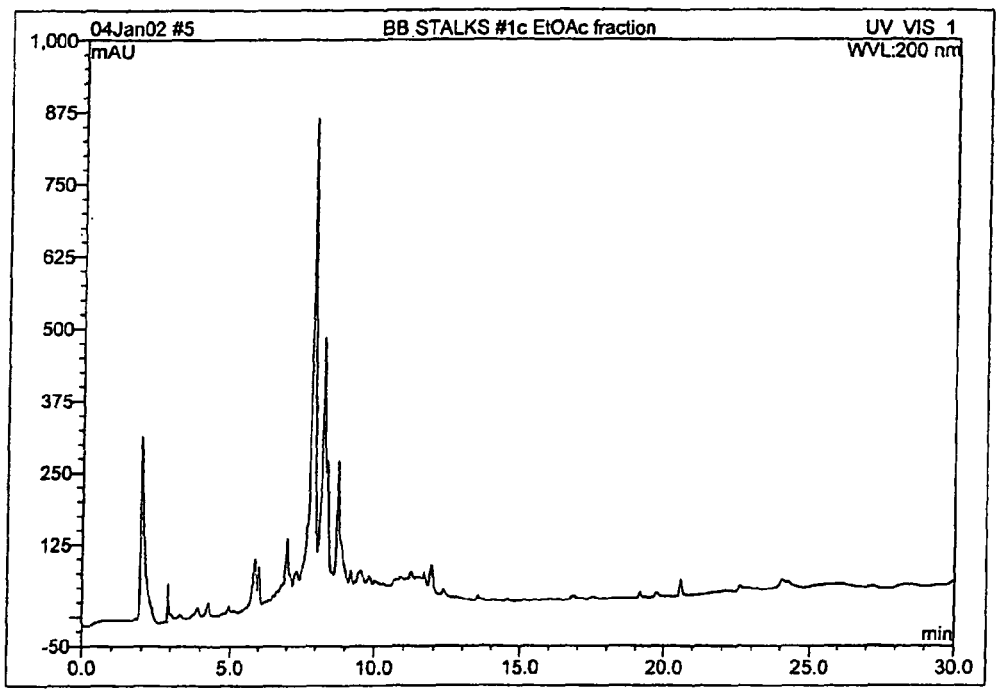
FIG. 26 is a graph which depicts an HPLC chromatogram at 200 nm of the total phenolics profile of wild Alaskan Blueberry stalks in ethyl acetate.
Figure 27:
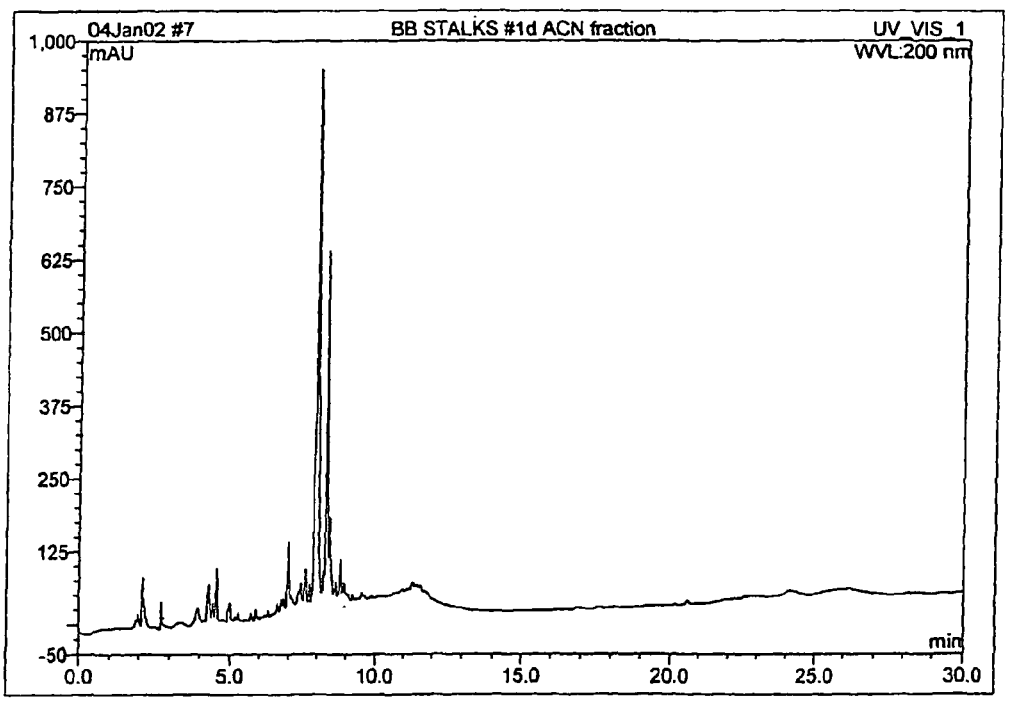
FIG. 27 is a graph which depicts an HPLC chromatogram at 200 nm of the total phenolics profile of wild Alaskan Blueberry stalks in acetonitrile.
Figure 28:
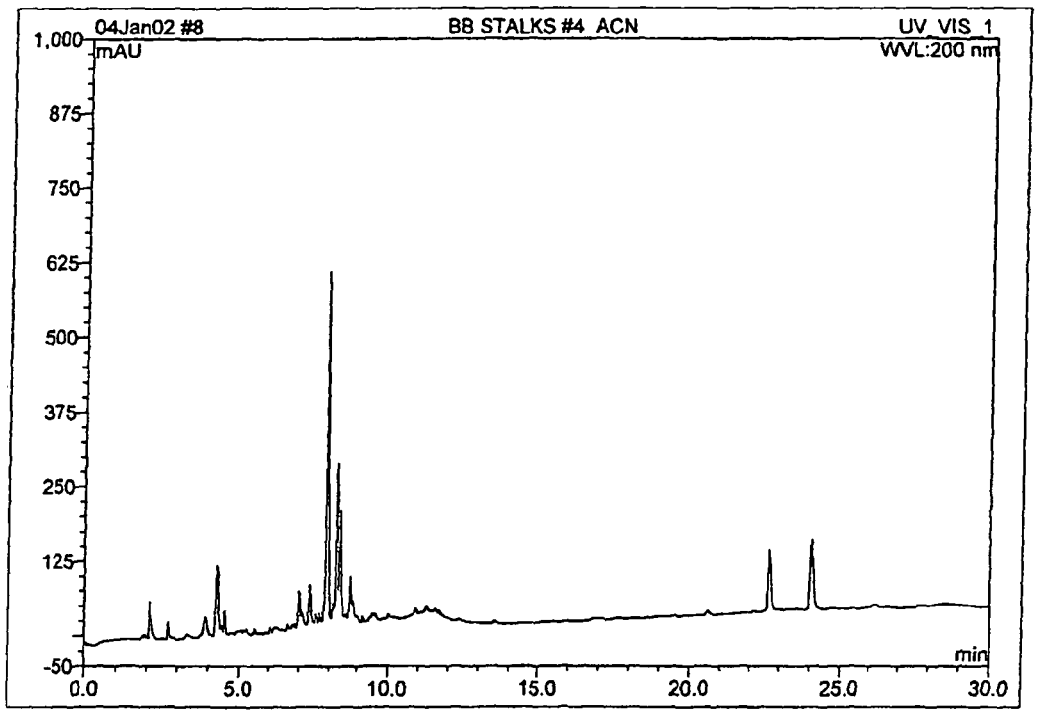
FIG. 28 is a graph which depicts an HPLC chromatogram at 200 nm of the total phenolics profile of wild Alaskan Blueberry stalks in acetonitrile.
Figure 29:
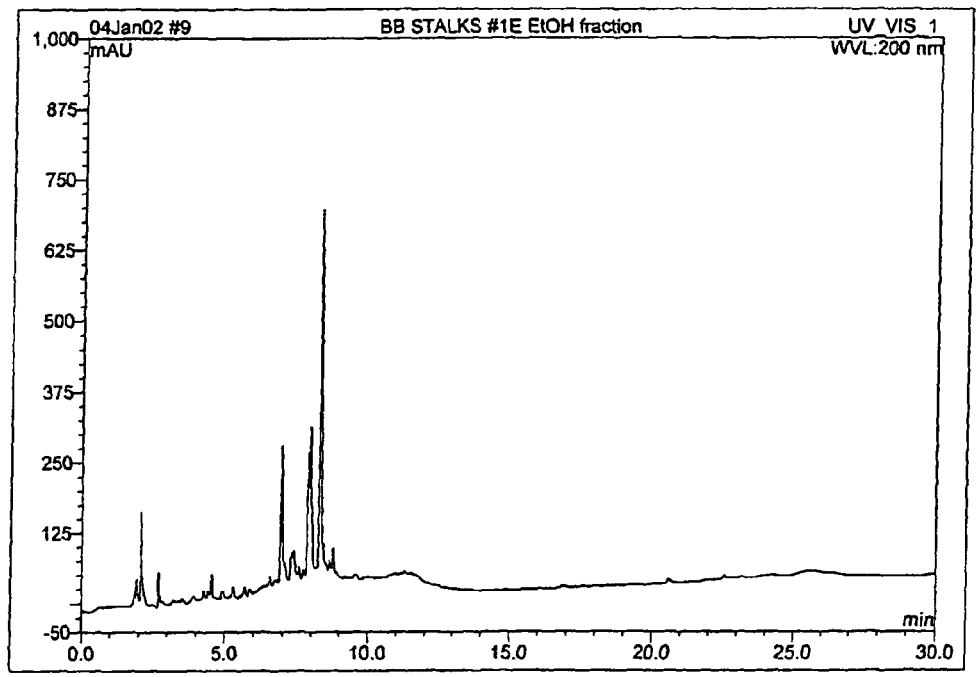
FIG. 29 is a graph which depicts an HPLC chromatogram at 200 nm of the total phenolics profile of wild Alaskan Blueberry stalks in ethanol.
Figure 30:
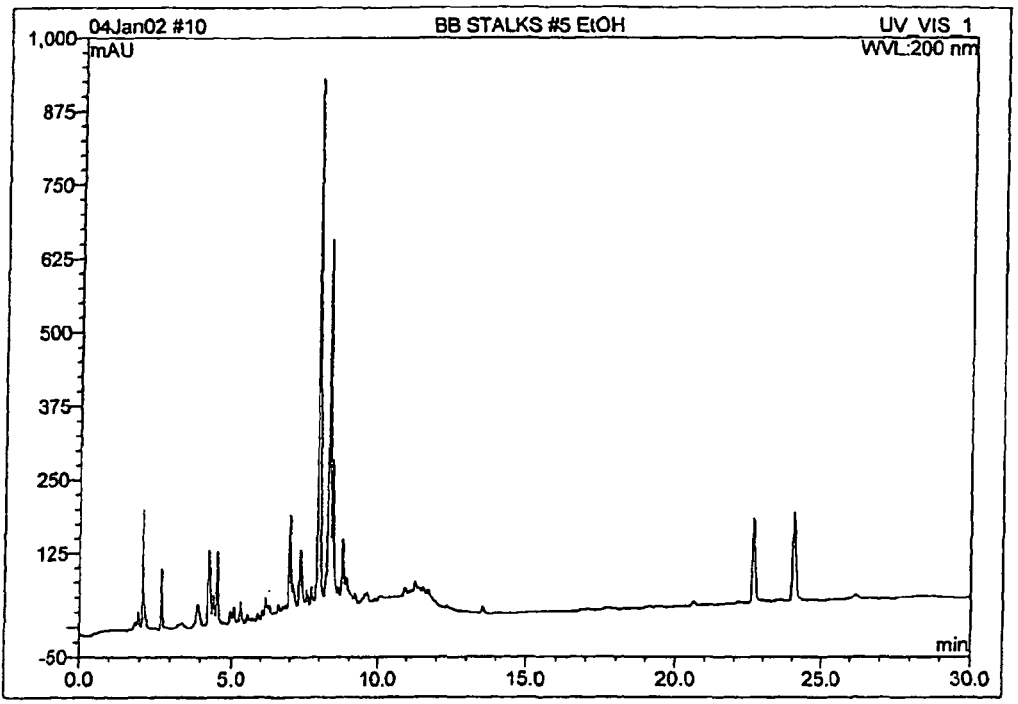
FIG. 30 is a graph which depicts an HPLC chromatogram at 200 nm of the total phenolics profile of wild Alaskan Blueberry stalks in ethanol.
Figure 31:
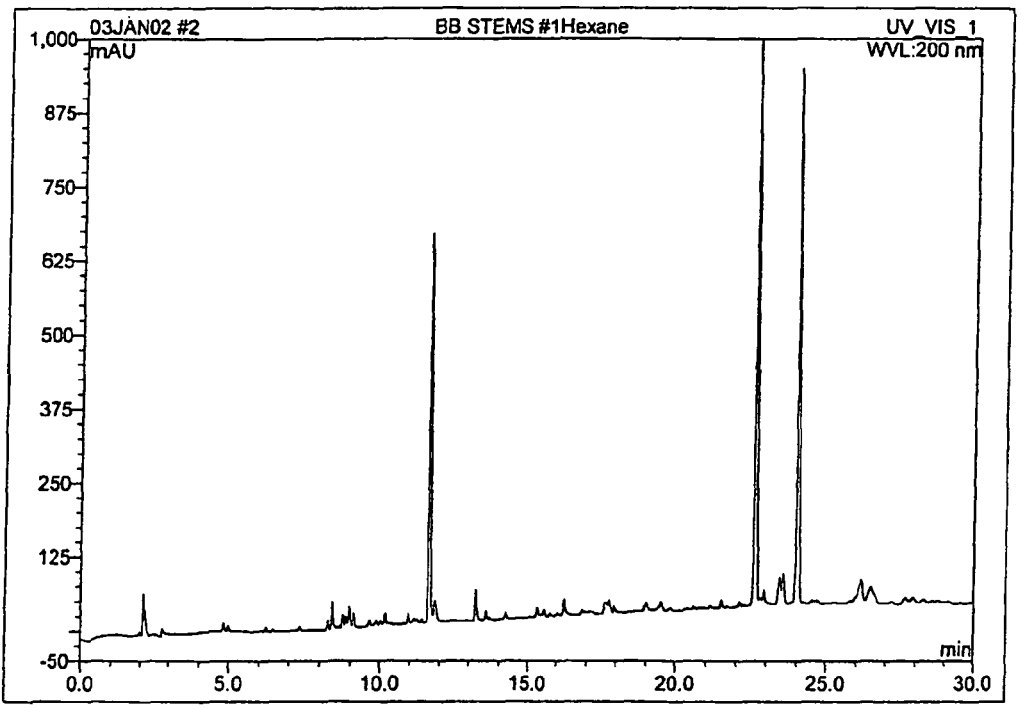
FIG. 31 is a graph which depicts an HPLC chromatogram at 200 nm of the total phenolics profile of wild Alaskan Blueberry stems in hexane.
Figure 32:
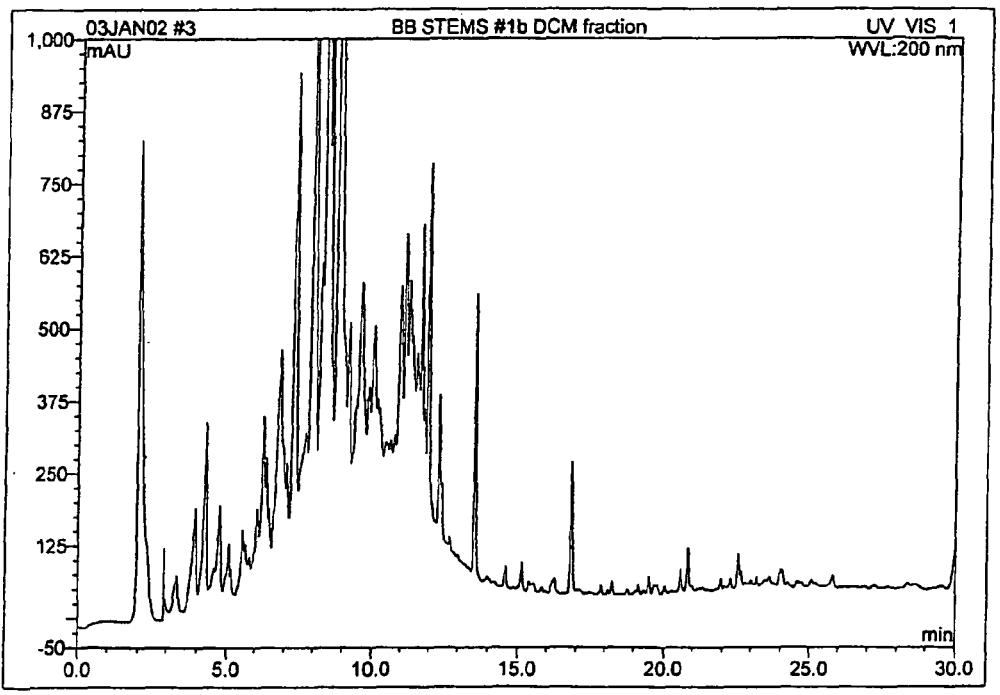
FIG. 32 is a graph which depicts an HPLC chromatogram at 200 nm of the total phenolics profile of wild Alaskan Blueberry stems in dichloromethane.
Figure 33:
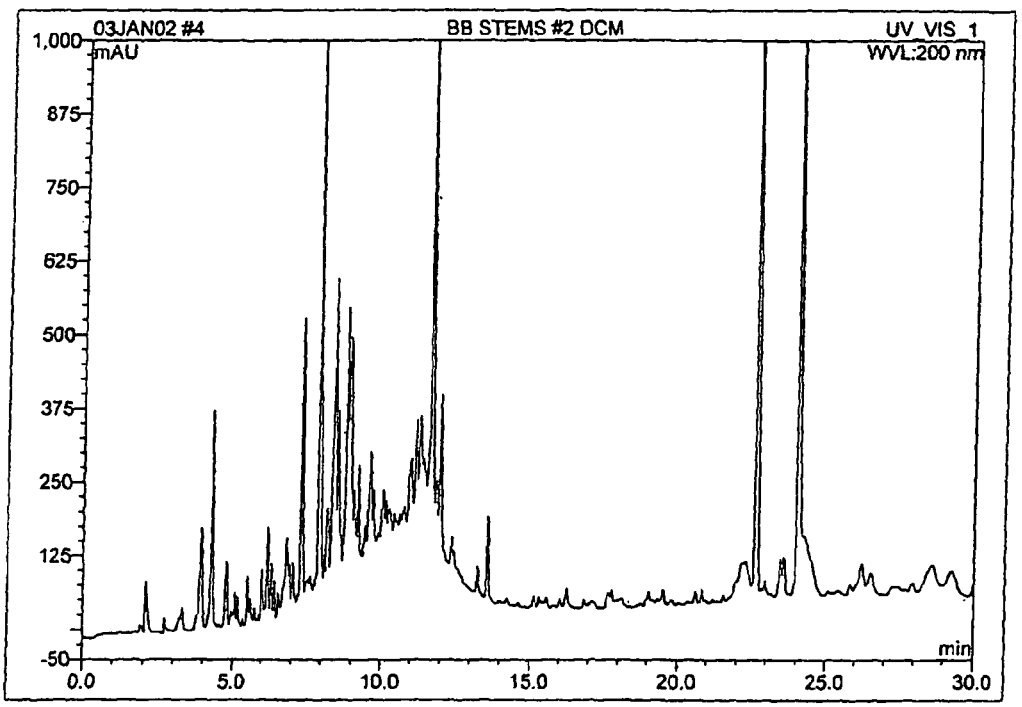
FIG. 33 is a graph which depicts an HPLC chromatogram at 200 nm of the total phenolics profile of wild Alaskan Blueberry stems in dichloromethane.
Figure 34:
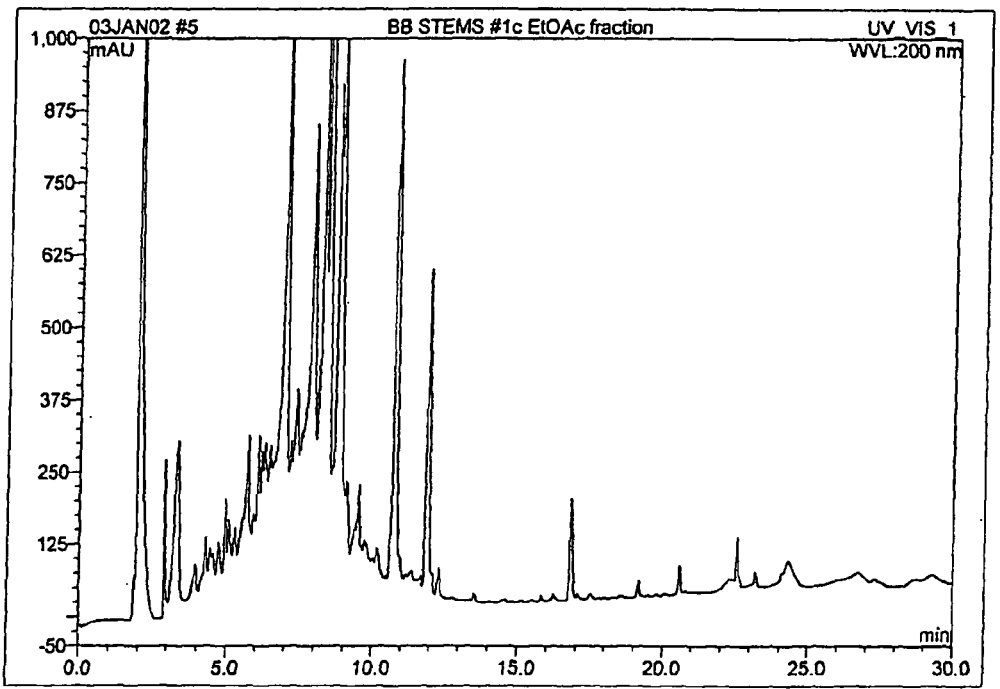
FIG. 34 is a graph which depicts an HPLC chromatogram at 200 nm of the total phenolics profile of wild Alaskan Blueberry stems in ethyl acetate.
Figure 35:
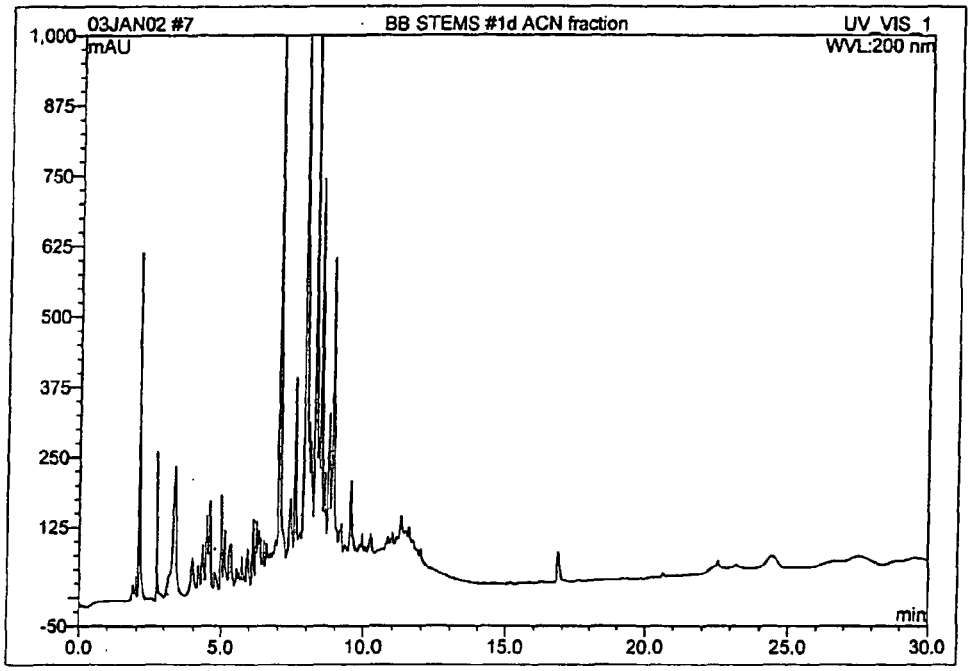
FIG. 35 is a graph which depicts an HPLC chromatogram at 200 nm of the total phenolics profile of wild Alaskan Blueberry stems in acetonitrile.
Figure 36:
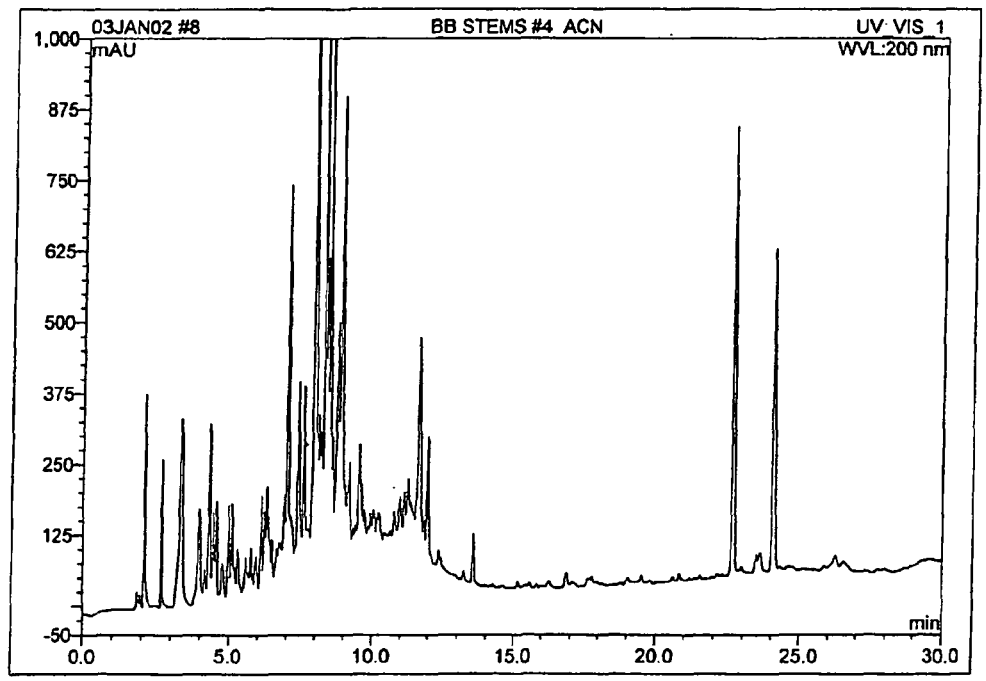
FIG. 36 is a graph which depicts an HPLC chromatogram at 200 nm of the total phenolics profile of wild Alaskan Blueberry stems in acetonitrile.
Figure 37:
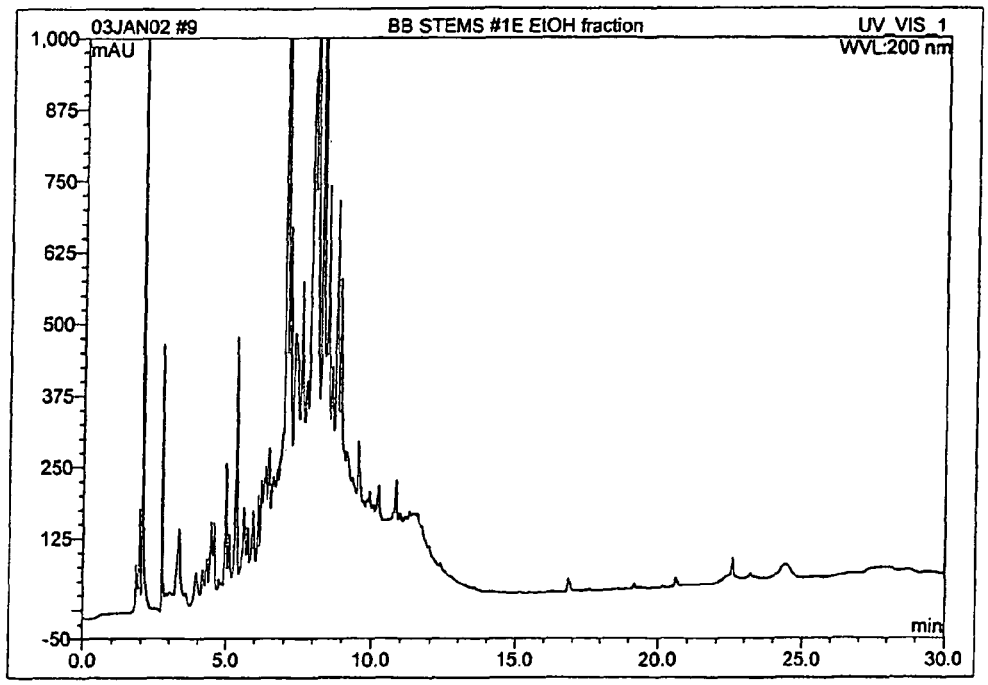
FIG. 37 is a graph which depicts an HPLC chromatogram at 200 nm of the total phenolics profile of wild Alaskan Blueberry stems in ethanol.
Figure 38:
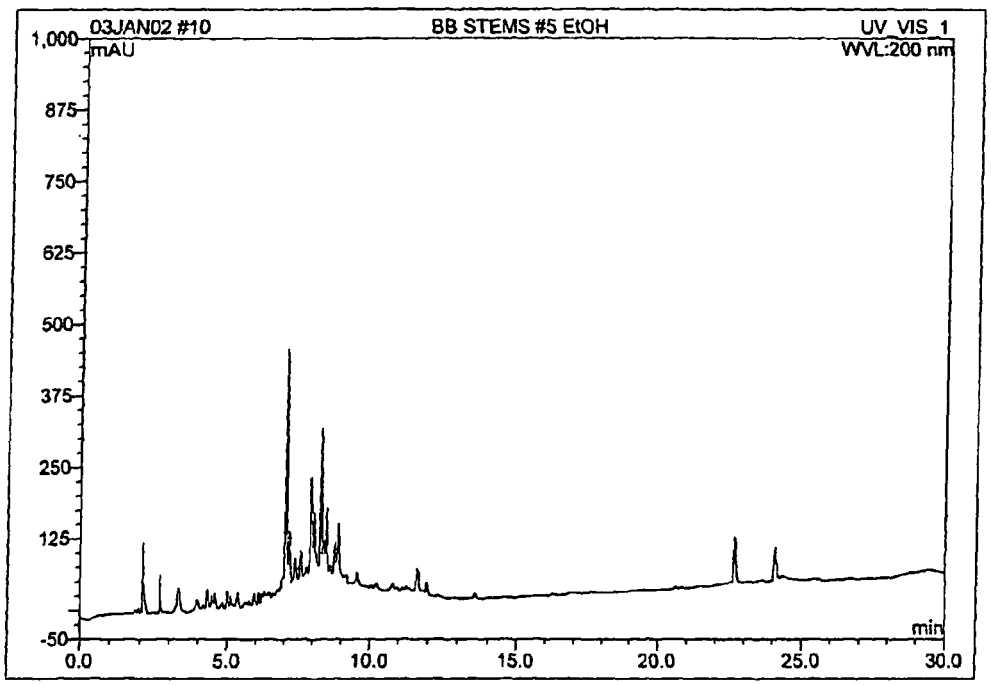
FIG. 38 is a graph which depicts an HPLC chromatogram at 200 nm of the total phenolics profile of wild Alaskan Blueberry stems in ethanol.
Figure 39:
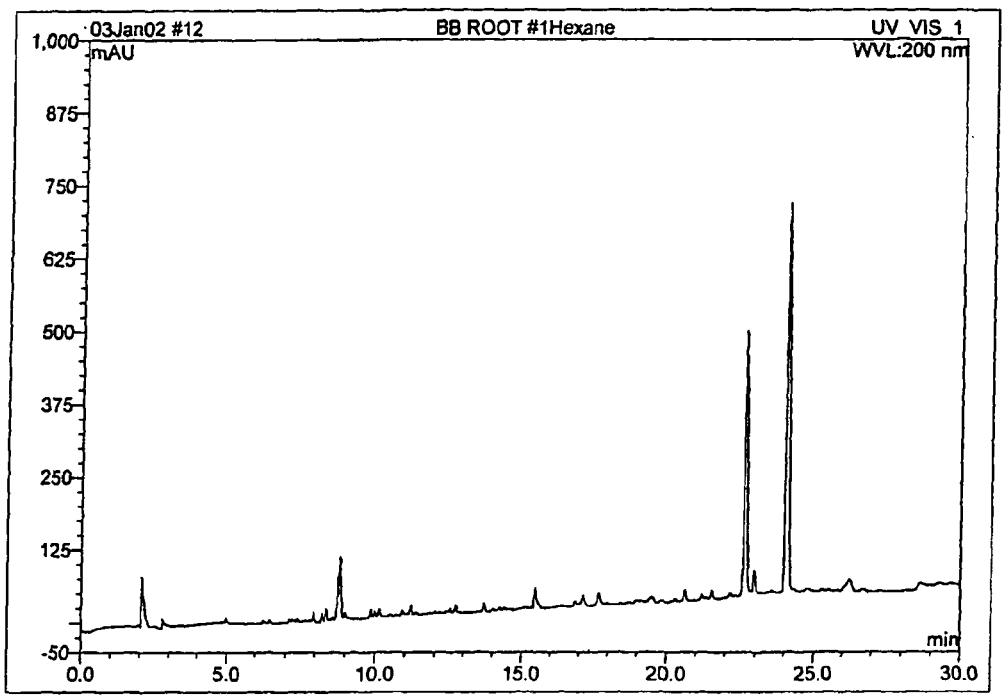
FIG. 39 is a graph which depicts an HPLC chromatogram at 200 nm of the total phenolics profile of wild Alaskan Blueberry root in hexane.
Figure 40:
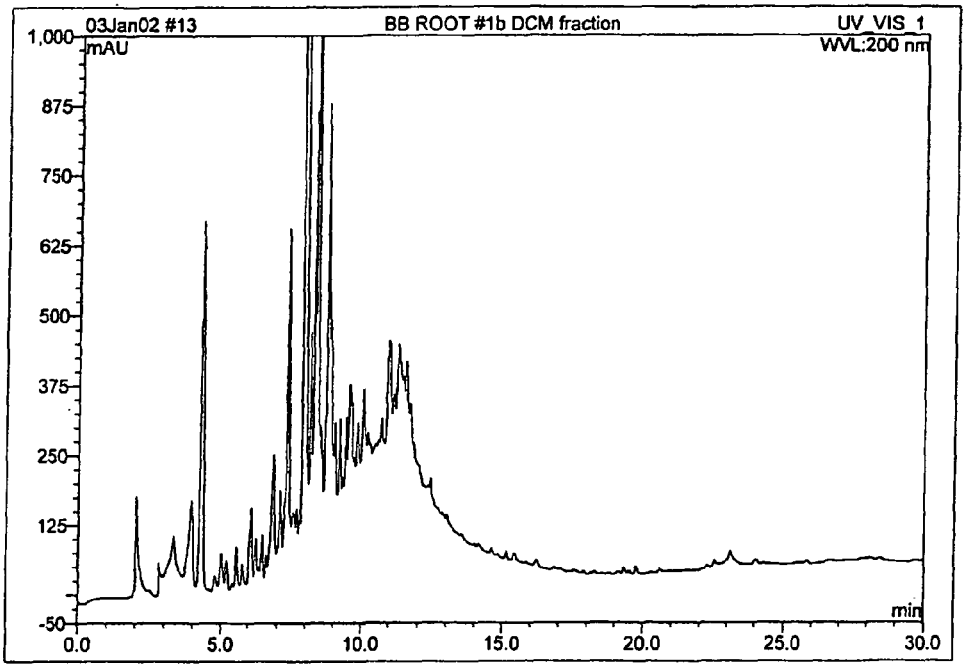
FIG. 40 is a graph which depicts an HPLC chromatogram at 200 nm of the total phenolics profile of wild Alaskan Blueberry root in dichloromethane.
Figure 41:
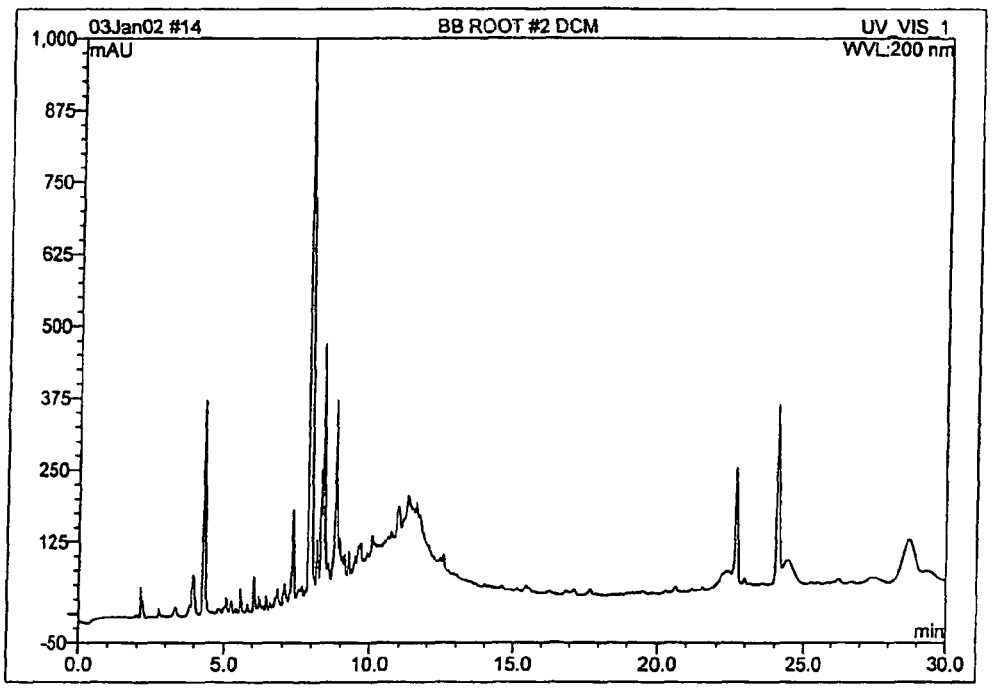
FIG. 41 is a graph which depicts an HPLC chromatogram at 200 nm of the total phenolics profile of wild Alaskan Blueberry root in dichloromethane.
Figure 42:
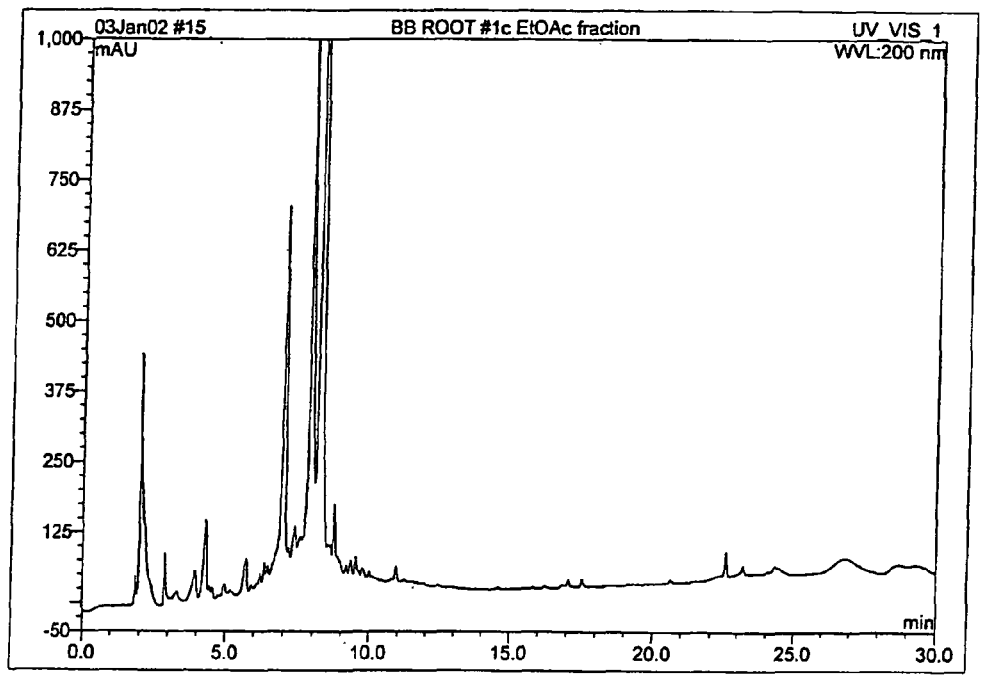
FIG. 42 is a graph which depicts an HPLC chromatogram at 200 nm of the total phenolics profile of wild Alaskan Blueberry root in ethyl acetate.
Figure 43:
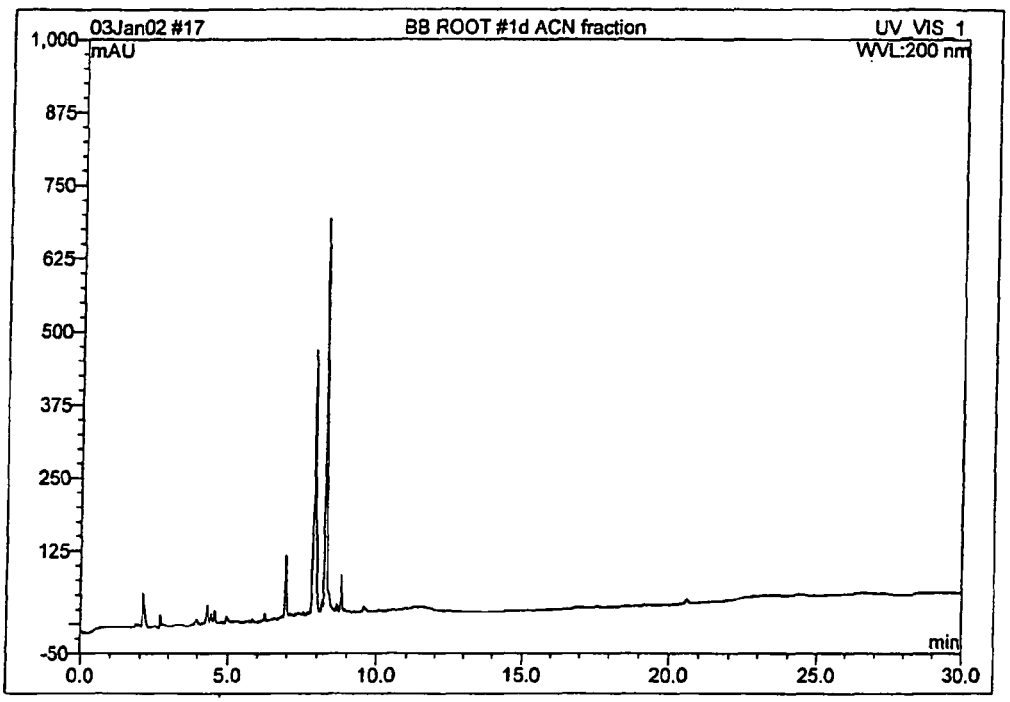
FIG. 43 is a graph which depicts an HPLC chromatogram at 200 nm of the total phenolics profile of wild Alaskan Blueberry root in acetonitrile.
Figure 44:
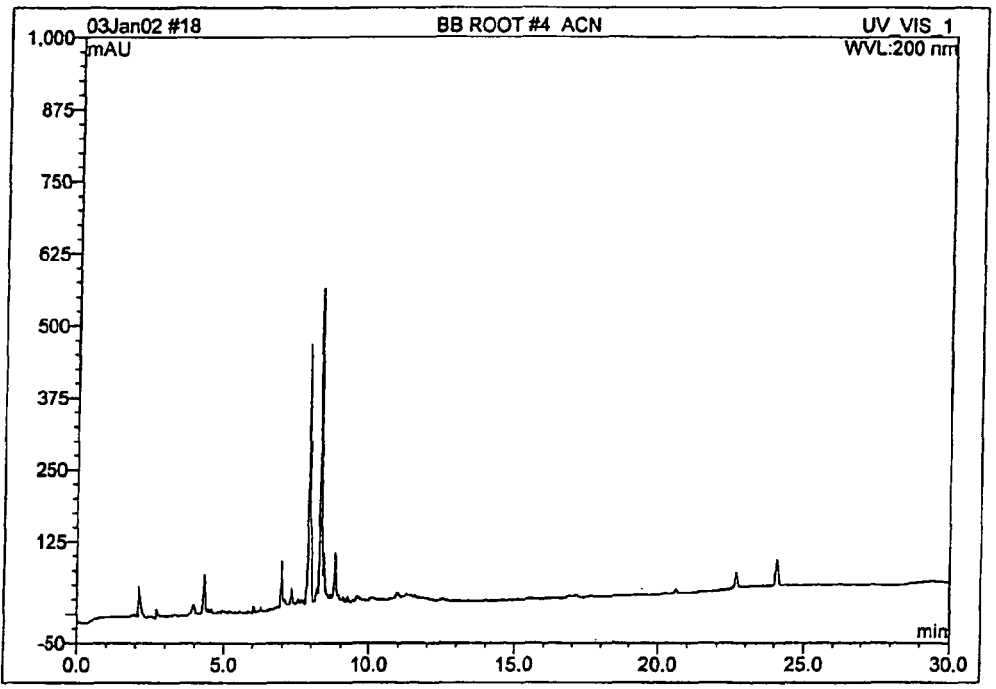
FIG. 44 is a graph which depicts an HPLC chromatogram at 200 nm of the total phenolics profile of wild Alaskan Blueberry root in acetonitrile.
Figure 45:
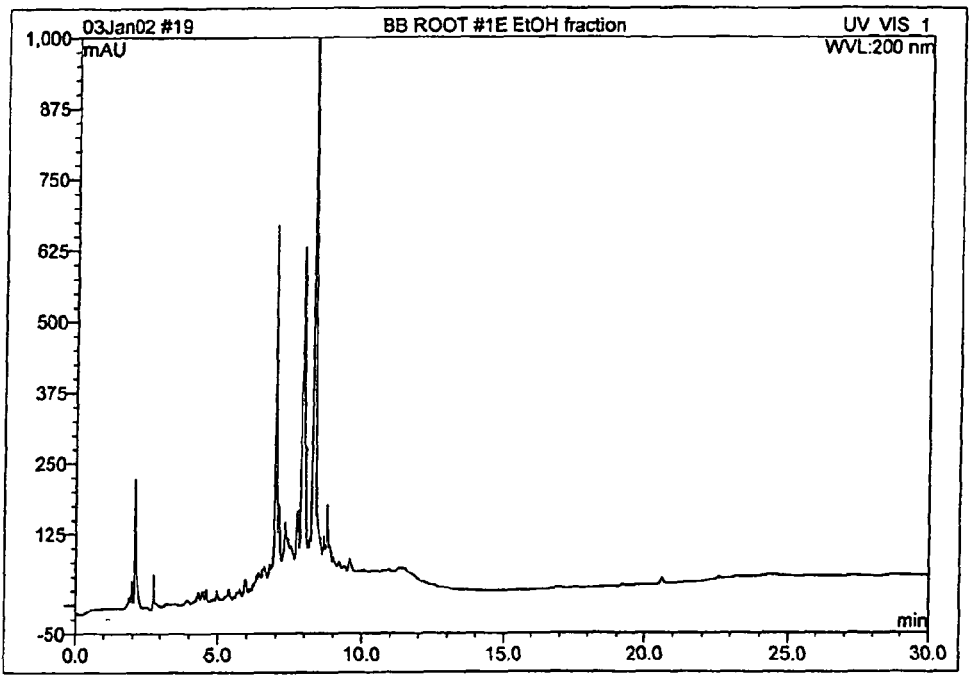
FIG. 45 is a graph which depicts an HPLC chromatogram at 200 nm of the total phenolics profile of wild Alaskan Blueberry root in ethanol.
Figure 46:
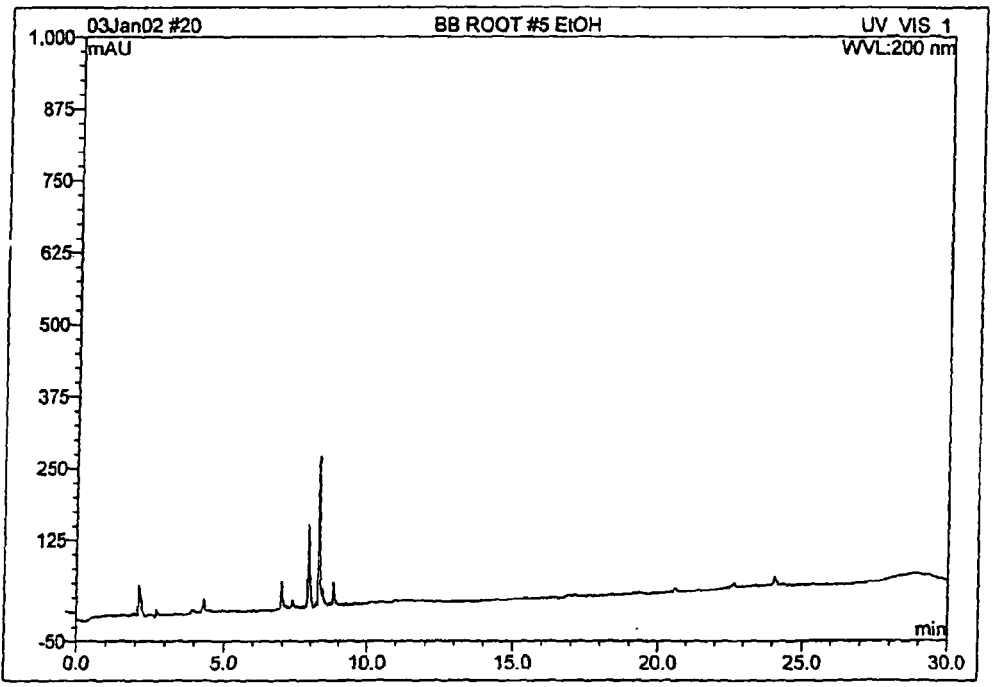
FIG. 46 is a graph which depicts an HPLC chromatogram at 200 nm of the total phenolics profile of wild Alaskan Blueberry root in ethanol.
Figure 47A:
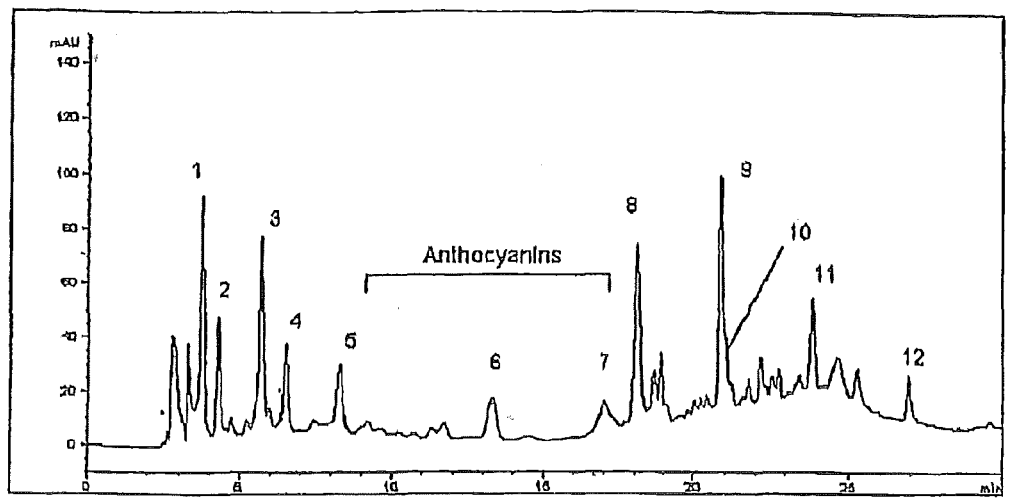
FIG. 47A is a graph and chart which depict an HPLC chromatogram at 280 nm of the total phenolics profile of wild Alaskan Blueberry root in ethyl acetate, and the characterization of phenolic compounds using RP-HPLC with UV detection.
Figure 47B:
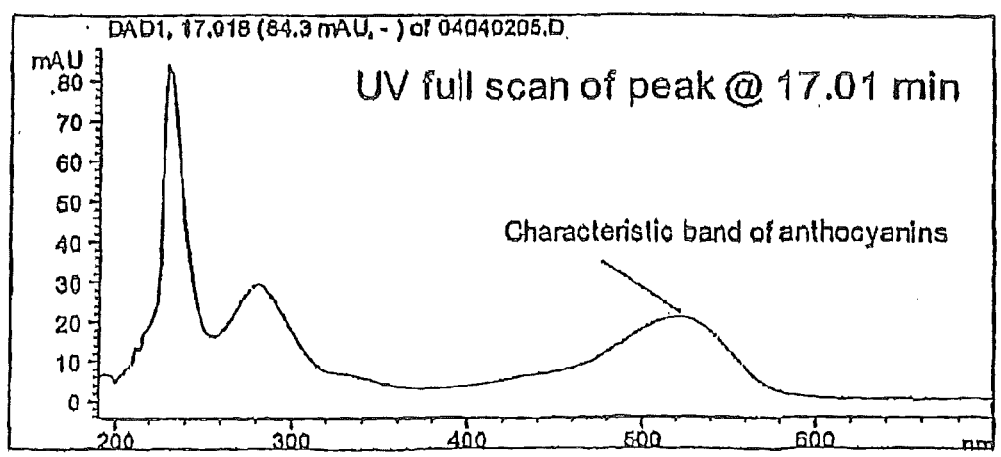
FIG. 47B is a graph which depicts an ultraviolet scan of peak 7 found in FIG. 47A

Comparing the antioxidant fingerprint profiles of Alaskan berries in FIG. 7 to a cultivated blueberry standard in FIG. 8. The magnitude of the detector response on the y-axis differs because the fingerprint of standard berries was from a concentrated extract and the Alaska berry profile is on the dehydrated material that was not extracted. Note the difference in retention times of the compounds.

Unlike other berries, the extremely high content of anthocyanins and polyphenols in high latitude berries, exemplified by Alaskan berries, enables the preparation of unique formulations as dehydrated whole foods, compared to others that require extraction to concentrate beneficial molecules. The berries of the inventive subject matter provide a meaningful dose raw or after only a mild refractance window drying step, without any additional processing or extraction. It should be noted that prior art extracts are produced by processes which require significant concentration of certain compounds of interest, excluding others naturally occurring in fruits, which do not provide a statistically meaningful dose in raw or simple dried form. The prior art extractions also exclude from the final product other molecules that are uncharacterized, yet beneficial. In the high latitude berries, exemplified by an Alaskan berry product, all of the substances are retained in essentially natural ratios, and said composition does not require an additional antioxidant element such as vitamin E for effectiveness.

As a "base" for product formulation, dehydrated *Vaccinium* rich in hydrophilic antioxidants, could be enhanced with oils, for example, *Oncorhynchus* (salmon) species, that naturally contain lipophilic Vitamin E and the carotenoid, astaxanthin, and omega-3 fatty acids. Thus, in another aspect of the inventive subject matter, a composition further comprises an oil from *Oncorhynchus* species.

In order to protect the compositions of the inventive subject matter, to improve delivery convenience, and to improve usability, the compositions of the inventive subject matter additionally comprise a physiologically acceptable carrier. Thus, in one alternate aspect of the invention, a physiologically acceptable carrier for oral administration in solid, paste, or powder form is selected from the group consisting of a softgel capsule and a two-piece capsule. In another alternate aspect of the invention, a physiologically acceptable carrier for oral administration in liquid form comprises one or more liquid(s) selected from the group consisting of water, fruit juice, milk, and/or one or more milk derivative(s). Of course, as will be apparent to one of ordinary skill in the art, such liquid carriers are merely exemplary and may be combined in various interchangeable formulations.

The novel compositions of the invention include a therapeutically effective amount of the active agent indicated above. This effective amount will generally comprise from about 0.1 mg to about 100 mg of the active agent per kilogram of patient body weight per day. This effective amount can vary depending upon the physical status of the patient and other factors well known in the art. Moreover, it will be understood that this dosage of active agent can be administered in a single or multiple dosage units to provide the desired therapeutic effect. If desired, other therapeutic agents can be employed in conjunction with those provided by the inventive subject matter.

The compounds of the invention are preferably delivered to the patient by means of a physiologically acceptable carrier. Such carriers are well known in the art and generally will be in either solid or liquid form. Solid form preparations which may be prepared according to the inventive subject matter include powders, tablets, dispersible granules, capsules, cachets and suppositories. In general, solid form preparations will comprise from about 5% to about 90% by weight of the active agent.

A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the viscous active compound. In tablets, the active compound is mixed with a carrier having the necessary binding properties in suitable proportions and compacted to the shape and size desired. Suitable solid carriers include magnesium carbonate, magnesium stearate, talc, sugar, lactose, pectin, dextrin, starch, gelatin, tragacanth, methylcellulose, sodium, carboxymethylcellulose, a low melting wax, cocoa butter, and the like. The term "preparation" is intended to include the formulation of the active compound with encapsulating materials as a carrier which may provide a capsule in which the active component, with or without other carriers, is surrounded by carrier, which is thus in association with it. Similarly, cachets are included.

Tablets, powders, cachets, softgels, and capsules can be used as solid dosage forms suitable for oral administration. If desired for reasons of convenience or patient acceptance, tablets prepared according to the invention may be provided in chewable form, using techniques well known in the art.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify. Liquid form preparations include solutions, suspensions, and emulsions. As an example may be mentioned water or water/propylene glycol solutions for parenteral injection.

Liquid preparations can also be formulated in solution in aqueous polyethylene glycol solution. Aqueous solutions suitable for oral use can be prepared by dissolving the active component in water and adding suitable colorants, flavors, stabilizers and thickening agents as desired. Aqueous suspensions suitable for oral use can be made my dispersing the finely divided active component in water with a viscous material, i.e., natural or synthetic gums, resins, methylcellulose, sodium carboxymethylcellulose, and other well known suspending agents. Liquid preparations may comprise up to 100% by weight of the subject active agent.

Also contemplated as suitable carriers are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing useful liquid form preparations may be water, isotonic water, ethanol, glycerine, propylene glycol, and the like as well as mixtures thereof. Naturally, the liquid utilized will be chosen with regard to the route of administration. For example, liquid preparations containing large amounts of ethanol are not suitable for parenteral use.

The preparation may also be in a unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The preparations of the invention may include one or more preservatives well known in the art, such as benzoic acid, sorbic acid, methylparaben, propylparaben and ethylenediaminetetraacetic acid. When utilized, preservatives are generally present in amounts up to about 1% and preferably from about 0.05 to about 0.5% by weight of the composition.

Useful buffers for purposes of the invention include citric acid-sodium citrate, phosphoric acid-sodium phosphate, and acetic acid-sodium acetate in amounts up to about 1% and preferably from about 0.05 to about 0.5% by weight of the composition. Useful suspending agents or thickeners include cellulosics like methylcellulose, carageenans like alginic acid and its derivatives, xanthan gums, gelatin, acacia, and microcrystalline cellulose in amounts up to about 20% and preferably from about 1% to about 15% by weight of the composition.

Sweeteners which may be employed include those sweeteners, both natural and artificial, well known in the art. Sweetening agents such as monosaccharides, disaccharides and polysaccharides such as xylose, ribose, glucose, mannose, galactose, fructose, dextrose, sucrose, maltose, partially hydrolyzed starch or corn syrup solids and sugar alcohols such as sorbitol, xylitol, mannitol and mixtures thereof may be utilized in amounts from about 10% to about 60% and preferably from about 20% to about 50% by weight of the composition. Water soluble artificial sweeteners such as saccharin and saccharin salts such as sodium or calcium, cyclamate salts, acesulfame-K, aspartame and the like and mixtures thereof may be utilized in amounts from about 0.001% to about 5% by weight of the composition.

Flavorants which may be employed in the products of the invention include both natural and artificial flavors, and mints such as peppermint, menthol, vanilla, artificial vanilla, chocolate, artificial chocolate, cinnamon, various fruit flavors, both individually and mixed, in amounts from about 0.5% to about 5% by weight of the composition.

Colorants useful in the inventive subject matter include pigments which may be incorporated in amounts of up to about 6% by weight of the composition. A preferred pigment, titanium dioxide, may be incorporated in amounts up to about 1%. Also, the colorants may include other dyes suitable for food, drug and cosmetic applications, known as F.D.&C. dyes and the like. Such dyes are generally present in amounts up to about 0.25% and preferably from about 0.05% to about 0.2% by weight of the composition. A full recitation of all F.D.&C. and D.&C. dyes and their corresponding chemical structures may be found in the Kirk-Othmer Encyclopedia of Chemical Technology, in Volume 5, at pages 857-884, which is accordingly incorporated by reference herein.

Useful solubilizers include alcohol, propylene glycol, polyethylene glycol and the like and may be used to solubilize the flavors. Solubilizing agents are generally present in amounts up to about 10%; preferably from about 2% to about 5% by weight of the composition.

Lubricating agents which may be used when desired in the instant compositions include silicone oils or fluids such as substituted and unsubstituted polysiloxanes, e.g., dimethyl polysiloxane, also known as dimethicone. Other well known lubricating agents may be employed.

It is not expected that compounds of the inventive subject matter will display significant adverse interactions with other synthetic or naturally occurring substances. Thus, a compound of the inventive subject matter may be administered in combination with other compounds and compositions useful for the same purposes. In particular the compounds of the inventive subject matter may be administered in combination with other compounds of the inventive subject matter.

The optimal formulations will be determined by one skilled in the art depending upon considerations such as the route of administration and desired dosage. See, for example, "Remington's Pharmaceutical Sciences", 18th ed. (1990, Mack Publishing Co., Easton, Pa. 18042), pp. 1435-1712, the disclosure of which is hereby incorporated by reference. Such formulations may influence the physical state, stability, rate of in vivo release, and rate of in vivo clearance of the present therapeutic agents of the invention.

Route(s) of Administration

The route(s) of administration of the compounds and compositions of the inventive subject matter are well known to those skilled in the art (see, for example, "Remington's Pharmaceutical Sciences", 18th Edition, Chapter 86, pp. 1581-

1592, Mack Publishing Company, 1990). The compounds and compositions may be administered orally, parenterally, by inhalation spray, topically, rectally, nasally, buccally, vaginally, or via an implanted reservoir in dosage formulations containing conventional non-toxic physiologically acceptable carriers, adjuvants, and vehicles. The term parenteral as used herein includes subcutaneous, intravenous, intramuscular, intraperitoneally, intrathecally, intraventricularly, intrasternal, and intracranial injection or infusion techniques.

To be effective therapeutically as central nervous system targets, the compounds and compositions should readily penetrate the blood-brain barrier when peripherally administered. Compounds which cannot penetrate the blood-brain barrier can be effectively administered by an intraventricular route.

The compounds and compositions may be administered in the form of sterile injectable preparations, for example, as sterile injectable aqueous or oleaginous suspensions. These suspensions may be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile, fixed oils are conventionally employed as solvents or suspending mediums. For this purpose, any bland fixed oil such as a synthetic mono- or di-glyceride may be employed. Fatty acids such as oleic acid and its glyceride derivatives, including olive oil and castor oil, especially in their polyoxyethylated versions, are useful in the preparation of injectables. These oil solutions or suspensions may also contain long-chain alcohol diluents or dispersants.

Additionally, in another aspect of the inventive subject matter, the compounds and compositions may be administered orally in the form of capsules, tablets, aqueous suspensions, or solutions. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening, flavoring, coloring agents, or combinations thereof. Delivery in an enterically coated tablet, caplet, or capsule, to further enhance stability and provide release in the intestinal tract to improve absorption, is the best mode of administration currently contemplated.

The compounds may also be administered rectally in the form of suppositories. These compositions can be prepared by mixing the drug with a suitable non-irritating excipient which is solid at room temperature, but liquid at rectal temperature and, therefore, will melt in the rectum to release the drug. Such materials include cocoa butter, beeswax, and polyethylene glycols.

Furthermore, the compounds may be administered topically, especially when the conditions addressed for treatment involve areas or organs readily accessible by topical application, including the lower intestinal tract. Suitable topical formulations can be readily prepared for such areas or organs. For example, topical application to the lower intestinal tract can be effected in a rectal suppository formulations (see above) or in suitable enema formulations.

It is envisioned that the continuous administration or sustained delivery of the compounds and compositions of the inventive subject matter may be advantageous for a given condition. While continuous administration may be accomplished via a mechanical means, such as with an infusion pump, it is contemplated that other modes of continuous or near continuous administration may be practiced. For example, such administration may be by subcutaneous or muscular injections as well as oral pills.

Techniques for formulating a variety of other sustained- or controlled-delivery means, such as liposome carriers, bio-erodible particles or beads and depot injections, are also known to those skilled in the art.

Dosage

For nutraceutical preparations, at least 1.5 mm dietary ORAC unit intake from substances occurring naturally in *Vaccinium* must comprise a single dose. Phytopharmaceutical preparations, designed to manage or treat a specific clinical condition, must contain at least 1.5 mm ORAC unit intake, calculated from the average concentrations and molecular weight of anthocyanin, polyphenolic, or proanthocyanidin molecules contained in the whole berry product or in specific extracts. Depending upon the condition being treated, dried or extracted preparations may contain up to 1500 mm ORAC unit intake from any or all of the anthocyanin, polyphenolic or proanthocyanidin molecules, or other active ingredients.

For phytopharmaceutical and pharmaceutical substances, dosage levels on the order of about 0.1 mg to about 100 mg per kilogram body weight of the active ingredient compositions are useful in the treatment of the above conditions, with preferred levels ranging on doses for reference man of 70 kg, from 7 mg per day to 7 g per day. For children under twelve, proportional doses reflecting body weight would be utilized. The compounds and compositions of the inventive subject matter may usually be given in two or three doses daily. Starting with a low dose once or twice daily and slowly working up to higher doses if needed is a preferred strategy. The amount of active ingredient that may be combined with the carrier materials to produce a single dosage form will vary depending upon the host treated and the particular mode of administration.

It is understood, however, that a specific dose level for any particular patient will depend upon a variety of factors, including the activity of the specific compound employed; the age, body weight, general health, sex and diet of the patient; the time of administration; the rate of excretion; drug combination; the severity of the particular disorder being treated; and the form of administration. One of ordinary skill in the art would appreciate the variability of such factors and would be able to establish specific dose levels using no more than routine experimentation.

Thus, the inventive subject matters also relates to a composition comprising berries obtained from one or more plant species of the genus *Vaccinium*, wherein said plant(s) is/are processed according to the following steps:
  (a) Exposed to one or more uninterrupted photoperiod(s) of at least about 18 hours to 24 hours per day for about 60 days during flowering and fruit setting;
  (b) Exposed to one or more uninterrupted photoperiod(s) of at least about 15 hours per day for about 30 days during fruit ripening and maturity;
  (c) Grown at least about 7 days past peak fruit ripeness;
  (d) Dried; and
  (e) Formulated into a therapeutic or nutritional composition having about 0.1 mg to about 100 mg per kilogram body weight of active ingredients.

Methods for Using the Inventive Compositions

The present invention relates to a method for treating a disorder in an animal, which comprises administering to said animal an effective amount of a composition comprising one or more berries, leaves, roots, and/or root barks obtained from one or more plant species of the genus *Vaccinium*,
wherein said plant(s) is/are grown under the following conditions:
i. Subject to one or more uninterrupted photoperiod(s) of at least about 18 hours to 24 hours per day for about 60 days during flowering and fruit setting; and
ii. Subject to one or more uninterrupted photoperiod(s) of at least about 15 hours per day for about 30 days during fruit ripening and maturity;
and wherein said disorder is selected from the group consisting of diabetes mellitus, inflammatory disorders, ulcers, viral diseases or disorders, microbial diseases or disorders, interstitial fluid formation, capillary resistance and permeability, decreased platelet aggregation, eyestrain, diabetic retinopathy, macular degeneration, cataracts, glaucoma, cancer, obesity, atherosclerosis, and cardiovascular disease; for improving visual function by promoting dark adaptation, enhancing the activity of metabolic enzymes in the retina, improving retinal regeneration, improving visual acuity, night vision, and contrast sensitivity; and for promoting wound-healing, normal formation of connective tissue, and strengthening of capillaries.

In another aspect of the inventive subject matter, a nutraceutical would be prepared from berries processed under any of the conditions described above, would be used alone for treatment of any of the aforementioned conditions.

In another aspect of the inventive subject matter, a nutraceutical would be prepared from berries processed under any of the conditions described above would be used in combination with *Oncorhynchus* oil for treatment of any of the aforementioned conditions.

In an alternate aspect of the inventive subject matter, a nutraceutical would be prepared from berries processed under any of the conditions described above would be used as a foundation, with out without *Oncorhynchus* oil, and with other appropriate substances for treatment of any of the aforementioned conditions.

In another aspect of the inventive subject matter, a nutraceutical would be prepared from berries with any or all combinations of leaves, stems, and roots and root bark processed under any of the conditions described above would be used alone for treatment of any of the aforementioned conditions.

In another aspect of the inventive subject matter, a nutraceutical would be prepared from berries with any or all combinations of leaves, stems, and roots and root bark processed under any of the conditions described above would be used in combination with *Oncorhynchus* oil for treatment of any of the aforementioned conditions.

In an alternate aspect of the inventive subject matter, a nutraceutical would be prepared from berries with any or all combinations of leaves, stems, and roots and root bark processed under any of the conditions described above would be used as a foundation, with out without *Oncorhynchus* oil, and with other appropriate substances for treatment of any of the aforementioned conditions.

Expected Health Benefits. In order to determine if there are health implications, one needs to understand 1) what phytochemicals in the fruit are responsible for the ORAC activities measured, 2) whether these substances can be absorbed, and 3) what physiological responses might be altered following their absorption.

Cancer: Fruits and vegetables contribute micronutrients such as ascorbic acid, beta carotene, and myriad other phytochemicals with antioxidant properties; the more closely a micronutrient was correlated with total vegetable and fruit intake, the more it appeared protective against cancer. A substantial body of experimental work has established that flavonoids can suppress carcinogenesis in animal models and there is considerable interest in the biological effects of these compounds at the cellular level.

The consumption of antioxidant-rich fruits and vegetables has been associated with lower incidence and lower mortality rates of cancer in several human cohort and case-control studies for all common cancer sites. Steinmetz and Potter reviewed the scientific literature from 206 human epidemiological studies and 22 animal studies on the relationship between vegetable and fruit consumption and the risk of cancer.

Evidence for a protective effect of greater vegetable and fruit consumption is consistent for cancers of the stomach, esophagus, lung, oral cavity and pharynx, endometrium, pancreas and colon. In an earlier review, approximately 200 studies were compiled and examined for the relationship between fruit and vegetable intake and cancers of the lung, colon, breast, cervix, esophagus, oral cavity, stomach, bladder, pancreas and ovary. For most cancer sites, individuals with low fruit and vegetable intake experienced about twice the risk of cancer compared with those with high intake. A statistically significant protective effect of fruit and vegetable consumption was found in 128 of 156 dietary studies in which results were expressed in terms of relative risk. Thus, the scientific evidence regarding a role for vegetable and fruit consumption in cancer prevention is generally consistent and is supportive of current dietary recommendations.

However, what is not clear from the available literature is what phytochemicals or antioxidants are responsible for the anticarcinogenicity and if specific fruits or vegetables might be more effective than others in preventing age-related diseases. The potentially antineoplastic effects of flavonoids not only include antioxidant activity, but induction of Phase II enzyme activity, inhibition of protein kinases and interactions with Type II estrogen binding sites. Flavonoids interact with cellular signal pathways controlling the cell cycle, differentiation and apoptosis.

Cardiovascular Disease: Epidemiological data, human clinical trials, and animal studies suggest that dietary antioxidants and diets rich in vegetables and fruits decrease cardiovascular disease and increase longevity. Consistent with the observed cancer chemoprotective effect, a highly significant negative association between intake of total fresh fruits and vegetables and ischemic heart disease mortality was reported in Britain and in the United States. A significant negative association was also reported between fruit and vegetable consumption and cerebrovascular disease mortality. The protective effects appear to be synergistic and are optimal when an array of different antioxidants are consumed simultaneously in naturally occurring quantities from different dietary plant sources.

The Anticipated Health Benefits of Anthocyanin Pigments and Polyphenolics. There is considerable anecdotal, animal, and epidemiological evidence that dietary flavanoids, including anthocyanins, proanthocyanidins, and various polyphenolics are expected to have preventive and therapeutic roles in a number of human diseases. Thus, naturally occurring polyphenolic compounds appear to have considerable potential for nutraceuticals and pharmaceutical uses as chemopreventive agents against neoplastic changes in the alimentary tract.

Anthocyanins. Anthocyanin pigments are responsible for the red, purple, and blue colors of many fruits, vegetables, cereal grains, and flowers. They have been the subject of investigation by botanists and plant physiologists because of their roles as pollination attractants and phytoprotective agents, and have been very useful in taxonomic studies. Food scientists and horticulturists continue to study these compounds because of their obvious importance to the color quality of fresh and processed fruits and vegetables. Over 300 structurally distinct anthocyanins have been identified in nature. Flavonols, flavan-3-ols, flavones, flavanones, and flavanonols are additional classes of flavonoids that differ in their oxidation state from the anthocyanins.

Other phenolic compounds. The polyphenolic profile of fruits and fruit juices is likely to include flavonols, free and esterified phenolic acids, and procyanthocyanidins or polymeric tannins. At least 5,000 naturally occurring polyphenolics have been identified, including over 2,000 flavonoids. Polyphenolics also contribute to food and beverage color. Proanthocyanidins and condensed tannins provide astringency and bitterness in tea and wine.

Early studies with rats suggest this antioxidant power from fruits translates to protection of cells and tissues. Dietary supplementation to rats of an extract from blueberries or strawberries has been shown to protect against the oxidative stress caused by 100% oxygen exposure.

The in vitro antiradical activity of anthocyanins and polyphenolics present in crude extracts of *Ribes, Rubus*, and *Vaccinium* genera on chemically-generated superoxide radicals as well as the inhibitory activity towards the enzyme xanthine oxidase have been studied. All the crude extracts demonstrated a remarkably high activity towards chemically-generated superoxide radicals. The activities were greater than those expected on the basis of the quantities of anthocyanins and polyphenolics present in the samples. All showed a certain inhibitory activity towards xanthine oxidase.

A number of studies have shown that mortality from coronary heart disease is inversely correlated with intake of flavonoids in the diet. Flavonoids are expected to also help prevent strokes. Through the much publicized "French paradox", the public has become aware that certain populations of red-wine drinkers in France and Italy have much lower rates of coronary heart disease than their North American and Northern European counterparts. It is widely accepted that red wine phenolics contribute at least partly to this beneficial effect. Experts have suggested that a recommended minimum daily requirement for dietary antioxidants be established.

Beneficial Properties of *Vaccinium* species. Bilberry and blueberry fruits of the *Vaccinium* genus are a rich source of anthocyanosides, a group of red to blue plant pigments, which exist as condensed products, for example glycosides, of anthocyanins known as anthocyanidins, combined usually with sugar(s) such as glucose, arabinose, and galactose. The 3-glucoside(s) and 3-galactoside(s) of delphinidin, malvidin, petunidin, cyanidin, and peonidin are the primary anthocyanins that have been identified in bilberries and blueberries.

The health-promoting effects of *Vaccinium* berries are likely accounted for primarily by the anthocyanins, but other polyphenols and phenolic acids, proanthocyanidins, and various flavonoid compounds are present in considerable concentrations. Anthocyanins are expected to have potential health benefits that are both independent of or in addition to their antioxidant effects, and most of the components present within *Vaccinium* are expected to have multiple health benefits which have not been well elucidated.

Bilberry. One of the most widely used *Vaccinium* supplements worldwide comes from *V. myrtillus*, a shrubby perennial that grows in the woods and forest meadows of Northern Europe and Asia, and to a lesser extent, in North America. *V. myrtillus* is a close relative of common North American species of commerce that include *V. angustifolium, V. corymbosum*, and *V. macrocarpon. V. myrtillus* has small, blue-black fruit and differs from an American blueberry in that its meat is also blue-black.

*V. myrtillus* scores highest among 50 fruits and vegetables in its ability to defuse damaging oxygen free radicals in the ORAC assay. In vitro assays show that bilberry extracts are expected to have an anticancer role from ability to induce the Phase II xenobiotic detoxification enzyme quinone reductase. The majority of inducer potency was contained in a hexane/chloroform subfraction, as opposed to the hydrophilic fraction rich in anthocyanins.

The leaf of the bilberry plant has also been used as a component of "diabetic" teas and is a rich source of chromium. High doses of bilberry leaves, greater than 480 mg/day, can be toxic. Traditional medicine tends to favor simple preparations of *V. myrtillus* that are not used in conjunction with other substances. Patent preparations typically contain a number of different components to enhance the value of *V. myrtillus*. An antihyperglycemic effect of the Antidiabetis herbal preparation containing "*Myrtilli folium*" as the principal ingredient has been demonstrated to lower blood glucose and fructosamine levels in alloxan-induced non-obese diabetic mice. In streptozotocin-induced diabetic rats, active consituent(s) of *V. myrtillus* leaves were found to consistently lower plasma glucose levels and to lower plasma triglyceride levels associated with dyslipidemia in diabetics. Another patent formulation uses Valerian root, *Valeriana officianalis*, either alone or in combination with other plant components, to be effective in lowering or otherwise regulating blood glucose concentrations.

The berries or extracts of the berries are believed to offer even greater benefit than the tea. Flavonoids, myrtillin and myricetin, and possibly other polyphenolics and tannins of bilberries have been shown to lower blood glucose. To determine the health-promoting effects of bilberry fruits several studies have been undertaken with a highly purified extract of *V. myrtillus* L., standardized to 36% anthocyanosides. In addition to its antioxidant activity, Myrtocyan$^R$ has been shown to 1) prevent or control interstitial fluid formation and contribute to controlling the blood flow redistribution in the microvascular network, 2) modulate capillary resistance and permeability, 3) improve visual function by promoting dark adaptation after dazzling, 4) promote wound-healing, 5) attenuate blood vessel thickening, such as atherosclerosis, and 6) possess anti-ulcer activity. Others corroborate that bilberry anthocyanosides are responsible for normal formation of connective tissue and strengthening of capillaries in the body, decreased platelet aggregation, and improved retinal regeneration.

Alterations in the capillary filtration of macromolecules are well documented in diabetic patients and experimental diabetes. Various flavonoids including anthocyanosides have been shown to be effective against experimentally induced capillary hyperfiltration. In *V. myrtillus* anthocyanoside treated streptozotocin-diabetic rats, interstitial albumin retention and the ratio of the amplitudes of the low- and high-frequency peaks, an index of lymphatic function were measured. Anthocyanosides appeared to be effective in preventing the increase in capillary filtration of albumin and the failure of lymphatic uptake of interstitial albumin in diabetic animals.

Bilberry anthocyanosides have been shown to improve symptoms and complications of IDDM and NIDDM related to the macrovasculature and microvasculature. A positive influence of bilberry anthocyanosides on the permeability and tendency of retinal microvasculature to hemorrhage has been observed. Diabetic retinopathy and macular degeneration that can lead to blindness is due to an abnormally increased synthesis of connective tissue in order to a) repair leaking capillaries and b) formation of new capillaries. Anthocyanosides help to prevent diabetics from injuries caused by malfunction of synthesis-activities throughout normal diabetic medical treatment such as laser coagulation therapy.

Anthocyanosides are expected also to improve vision by enhancing the activity of metabolic enzymes in the retina. Diabetic cataracts are caused by an elevation of polyols within the lens of the eye catalyzed by the enzyme aldose reductase. Bilberry is expected to diminish or help prevent cataracts through its flavonoids, particularly quercetin and derivatives, which are potent inhibitors aldose reductase. In addition, pathophysiological mechanisms of cataract formation include deficient glutathione levels contributing to a faulty antioxidant defense system within the lens of the eye. Similar to patients with cataracts, those with glaucoma typically have compromised antioxidant defense systems, and are expected to benefit from anthocyanoside supplements.

Bilberry anthocyanosides enhance the regeneration of rhodopsin or visual purple, an eye protein necessary for vision in dim light or at night, and have been used to improve visual acuity and night vision. Although a report of improved night vision among air traffic controllers supports these claims, other recent well-controlled clinical trials did not show any benefit on night visual acuity or contrast sensitivity in subjects with normal vision.

Blueberry. Research is showing that blueberries contain a number of compounds that have medicinally beneficial properties. The earliest recorded use of blueberry for medicinal purposes dates from the Middle Ages, and it has been used in European folk medicine since the 16th century. Some of its reported medicinal benefits include antioxidant properties, anti-cancer activity, reducing heart disease risk, strengthening collagen, regulating blood sugar, improving night vision, preventing urinary tract infections, reducing replication of the HIV virus, and treating diarrhea. Blueberry leaf tea has a long history as a folk treatment for diabetes and, in animal studies, extracts from leaves decreased blood glucose and blood triglyceride levels. In normal and diabetic dogs, oral administration reduces hyperglycemia, even when glucose is injected intravenously at the same time.

Crude extracts of lowbush blueberry, and other *Vaccinium* species such as cranberry and lingonberry, are active inhibitors of the cell division regulatory enzyme, ornithine decarboxylase activity. The greatest activity in these extracts appeared to be contained in the polymeric proanthocyanidin fractions of the lowbush blueberry. The anthocyanidin and ethyl acetate extracts of these *Vaccinium* species, as well as bilberry, are either inactive or relatively weak inhibitors of ornithine decarboxylase activity. Proanthocyanidins from blueberry, as well as cranberry, are also effective inhibitors of *Escherichia coli* adhesion factor and help to prevent urinary tract infections.

A blueberry extract was examined in a Japanese study for effects on eyestrain and fatigue. Researchers employed critical fusion frequency of flicker test involving rapid light flickering in front of the patient to determine how quickly the eye adjusts, and a visual analogue scale to rank the degree to which the eyes are tired. Blueberry extract had a positive effect on tired eyes more than on any other symptom.

In experimental hyperoxia in rats, a redistribution of systemic antioxidants between serum and pleural effusion and an increase in capillary permeability occurs. Of various fruits and vegetable extracts tested, only the blueberry extract was effective in alleviating the hyperoxia-induced redistribution of antioxidants between tissues. Dietary consumption of polyphenolics from blueberries was found to enhance significantly red blood cell resistance to hydrogen peroxide, 100 mM, induced reactive oxygen species production.

Research that indicates increasing vulnerability to oxidative stress with aging, leading to cancer and cardiovascular disease, also demonstrates that age-related declines in neuronal and cognitive function and development of neurodegenerative diseases such as Alzheimer's disease or vascular dementia may be superimposed upon a vulnerable neuronal environment. Among the most effective agents that antagonized neuronal cell OSV are multiple polyphenolics found in blueberry extract, and other fruits, with high antioxidant activity.

Products Produced by the Process of the Inventive Subject Matter

The present invention further relates to a product produced by the process of:
 i. Growing a plant of a species of the genus *Vaccinium* under the following conditions:
  (a) Subject to one or more uninterrupted photoperiod(s) of at least about 18 hours to 24 hours per day for about 60 days during flowering and fruit setting,
  (b) Subject to one or more uninterrupted photoperiod(s) of at least about 15 hours per day for about 30 days during fruit ripening and maturity, and
  (c) Grown at least about 7 days past peak fruit ripeness;
 ii. Harvesting berries, leaves, roots, and/or root barks from said plant; and
 iii. Drying said berries, leaves, roots, and/or root barks from said plant.

In another aspect of the inventive subject matter, the growing step and/or the harvesting step of said process additionally comprises exposing said plant(s) to one or more freeze cycle(s) during growth and/or post-harvest.

In another aspect of the inventive subject matter, the harvesting and drying steps are limited to the berries of said plant(s).

EXAMPLES

The following examples are illustrative of the inventive subject matter and are not intended to be limitations thereon. Unless otherwise indicated, all percentages are based upon 100% by weight of the final composition.

Example 1

Preparation of Berry Compositions

The following example illustrates the preparation of a preferred active agent in several compositions provided according to the inventive subject matter.

Mature, high latitude berries of the genus *Vaccinium* are collected from wild stands. Samples of plant material from each of the stands are retained for a voucher specimen. The berries are frozen for a minimum duration of 24 hours prior to further processing. Frozen berries and juice extruded during thaw are ground together to form a thick, spreadable puree. The puree is applied to the conveyor belt of a Refractance Window dryer for evaporation. The resulting granular material is used directly or is further processed for various product requirements.

For use in functional foods, the granular material is incorporated into products including but not limited to bakery goods and breakfast, snack, sports, calorie-reduced and meal replacement bars, breakfast cereals, dairy-based products, frozen fruit products, jams, jellies, syrups, sauces, and condiments.

For use in dietary supplements, the granular material is milled to a sufficiently fine powder for respective applications including but not limited to fruit and berry-based beverages, such as tonics, sports drinks, and health-related beverages, in tablets or chews, and for filling softgel and 2-piece hard shell capsules.

For use as a phytopharmaceutical or for management of specific disease states, the milled powder may be used alone or formulated with other ingredients. The fresh berries and derivative granular or milled powder, leaves, stems, bark, roots, and root barks may also be extracted to concentrate certain components for prevention or management of specific disease conditions.

For use as a pharmaceutical, the fresh berries and granular material or milled powder comprised of berries, flowers, leaves, stems, bark, roots, and root barks may be extracted for preparation of pure, novel, small molecules with specific therapeutic properties.

Example 2

Treating Diabetes

The following example illustrates use of a composition provided according to the inventive subject matter for treating Type I Diabetes.

A composition of the inventive subject matter was given to a diabetic individual with instructions to consume 1 teaspoon in the morning at fasting, and then to monitor blood glucose within the hour. The blood glucose levels at fasting of said individual normally run 120-140 mg/dl. On three separate occasions, said individual reported a drop to 35, 27, and less than 12 mg/dl, respectively.

Example 3

Treating Hyperglycemia

A patient presents for treatment of hyperglycemia. The patient is administered an inventive composition having an effective amount of myricetin and its glucoside, documented hypoglycemic agents which are significant components of said composition. The patient undergoes the procedure well, without complication, and the inventive composition is successful in reducing blood sugar, avoiding more complex, expensive, and potentially side-effect-producing treatment.

Example 4

*Vaccinium* Extracts

The fresh or dried leaves of *Vaccinium* species are boiled to extract water-soluble substances to make a decoction, or are steeped or soaked without boiling to extract water-soluble substances to make an infusion. The resulting decoctions and infusions are used as a urinary tract antiseptic, anti-tubercular agent, and hypoglycemic agent. Applicant expects that the leaves are most potent when the plant is in flower, and that ORAC values are higher at that time for leaves; it is believed that polyphenolics contribute to potency and high ORAC values.

The invention being thus described, it will be obvious that the same may be modified or varied in many ways. Such modifications and variations are not to be regarded as a departure from the spirit and scope of the invention and all such modifications and variations are intended to be included within the scope of the following claims.

I claim:

1. A method for treating inflammation linked to a disorder in an animal, which comprises the steps of
   a) obtaining one or more plants selected from the group consisting of *V. alaskensis, V. axillare, V. caespitosum, V. caespitosum* var. *paludicola, V. membranaceum, V. parvifolium, V. ovalifolium, V. oxycoccus, V. shikokianum, V. uliginosum* subsp. *alpinum, V. uliginosum* var. *salicinum, V. uliginosum* subsp. *microphyllum, V. vitis-idaea* subsp. *minus*, and *V. vitis-idaea* subsp.*vitis- idaea*, wherein said one or more plants have grown under the following conditions:
      i. Subject to one or more uninterrupted photoperiod(s) of at least about 18 hours to 24 hours per day for about 60 days during flowering and fruit setting;
      ii. Subject to one or more uninterrupted photoperiod(s) of at least about 15 hours per day for about 30 days during fruit ripening and maturity; and
      iii. Subject to growth for at least 7 days past peak fruit ripeness;
   (b) drying parts comprising one or more berries, and optionally one or more members of the group consisting of leaves, roots, and root bark, of said one or more plants;
   (c) milling said dried parts of said one or more plants into a fine powder;
   (d) formulating a composition comprising the fine powder in dosage form; and
   (e) administering to said animal an effective amount of the composition;
      wherein said disorder is diabetes mellitus; wherein said composition comprises, at least in part, a metabolite produced by one or more stress-related phenylpropanoid pathway(s); and wherein said administering is accomplished orally.

2. A method for treating inflammation linked to a disorder in an animal, which comprises the steps of
   (a) obtaining one or more plants selected from the group consisting of *V. alaskensis, V. axillare, V. caespitosum, V. caespitosum* var. *paludicola, V. membranaceum, V. parvifolium, V. ovalifolium, V. oxycoccus, V. shikokianum, V. uliginosum* subsp. *alpinum, V. uliginosum* var. *salicinum, V. uliginosum* subsp. *microphyllum, V. vitis-idaea* subsp. *minus*, and *V. vitis-idaea* subsp.*vitis-idaea*, wherein said one or more plants have grown under the following conditions:
      i. Subject to one or more uninterrupted photoperiod(s) of at least about 18 hours to 24 hours per day for about 60 days during flowering and fruit setting;
      ii. Subject to one or more uninterrupted photoperiod(s) of at least about 15 hours per day for about 30 days during fruit ripening and maturity; and
      iii. Subject to growth for at least 7 days past peak fruit ripeness;
   (b) driving parts comprising one or more berries, and optionally one or more members of the group consisting of leaves, roots, and root bark, of said one or more plants;
   (c) milling said dried parts of said one or more plants into a fine powder;
   (d) formulating a composition comprising the fine powder in dosage form; and
   (e) administering to said animal an effective amount of the composition;

wherein the disorder is cancer; wherein said composition comprises, at least in part, a metabolite produced by one or more stress-related phenylpropanoid pathway(s); and wherein said administering is accomplished orally.

3. A method for treating inflammation linked to a disorder in an animal, which comprises the steps of
(a) obtaining one or more plants selected from the group consisting of *V. alaskensis, V. axillare, V. caespitosum, V. caespitosum* var. *paludicola, V. membranaceum, V. parvifolium, V. ovalifolium, V. oxycoccus, V. shikokianum, V. uliginosum* subsp. *alpinum, V. uliginosum* var. *salicinum*, and *V. uliginosum* subsp. *microphyllum*,
wherein said one or more plants have grown under the following conditions:
 i. Subject to one or more uninterrupted photoperiod(s) of at least about 18 hours to 24 hours per day for about 60 days during flowering and fruit setting;
 ii. Subject to one or more uninterrupted photoperiod(s) of at least about 15 hours per day for about 30 days during fruit ripening and maturity; and
 iii. Subject to growth for at least 7 days past peak fruit ripeness;
(b) drying parts comprising one or more berries, and optionally one or more members of the group consisting of leaves, roots, and root bark, of said one or more plants;
(c) milling said dried parts of said one or more plants into a fine powder;
(d) formulating a composition comprising the fine powder in dosage form; and
(e) administering to said animal an effective amount of the composition;
wherein said disorder is diabetes mellitus; wherein said composition comprises, at least in part, a metabolite produced by one or more stress-related phenylpropanoid pathway(s); and wherein said administering is accomplished orally.

4. A method for treating inflammation linked to a disorder in an animal, which comprises the steps of
(a) obtaining or more plants selected from the group consisting of *V. alaskensis, V. axillare, V. caespitosum, V. caespitosum* var. *paludicola, V. membranaceum, V. parvifolium, V. ovalifolium, V. oxycoccus, V. shikokianum, V. uliginosum* subsp. *alpinum, V. uliginosum* var. *salicinum*, and *V. uliginosum* subsp. *microphyllum*,
wherein said one or more plants have grown under the following conditions:
 i. Subject to one or more uninterrupted photoperiod(s) of at least about 18 hours to 24 hours per day for about 60 days during flowering and fruit setting;
 ii. Subject to one or more uninterrupted photoperiod(s) of at least about 15 hours per day for about 30 days during fruit ripening and maturity; and
 iii. Subject to growth for at least 7 days past peak fruit ripeness;
(b) drying parts comprising one or more berries, and optionally one or more members of the group consisting of leaves, roots, and root bark, of said one or more plants;
(c) milling said dried parts of said one or more plants into a fine powder;
(d) formulating a composition comprising the fine powder in dosage form: and
(e) administering to said animal an effective amount of the composition;
wherein said disorder is cancer; wherein said composition comprises, at least in part, a metabolite produced by one or more stress related phenylpropanoid pathway(s); and wherein said administering is accomplished orally.

* * * * *